(12) United States Patent
Wegenkittl et al.

(10) Patent No.: US 7,787,679 B2
(45) Date of Patent: Aug. 31, 2010

(54) STUDY NAVIGATION SYSTEM AND METHOD

(75) Inventors: Rainer Wegenkittl, Sankt Poelten (AT);
Donald K. Dennison, Waterloo (CA);
John J. Potwarka, Waterloo (CA);
Lukas Mroz, Vienna (AT); Scott Gerald Galbari, Narragansett, RI (US); Armin Kanitsar, Vienna (AT); Gunter Zeilinger, Vienna (AT)

(73) Assignee: Agfa HealthCare Inc., Toronto (CA)

( * ) Notice: Subject to any disclaimer, the term of this patent is extended or adjusted under 35 U.S.C. 154(b) by 548 days.

(21) Appl. No.: 11/562,850

(22) Filed: Nov. 22, 2006

(65) Prior Publication Data
US 2008/0118120 A1 May 22, 2008

(51) Int. Cl.
G06K 9/00 (2006.01)
G06K 9/54 (2006.01)
G06K 9/60 (2006.01)
G06F 3/048 (2006.01)

(52) U.S. Cl. ................ 382/128; 382/305; 707/821; 715/835

(58) Field of Classification Search ......... 382/103–105, 382/107, 153, 291, 128–132, 305; 348/143–160, 348/169–172; 707/821–831; 715/835–838
See application file for complete search history.

(56) References Cited

U.S. PATENT DOCUMENTS

| | | | | |
|---|---|---|---|---|
| 5,537,530 A * | 7/1996 | Edgar et al. | ............... | 715/723 |
| 5,818,439 A * | 10/1998 | Nagasaka et al. | ............... | 725/87 |
| 6,154,771 A * | 11/2000 | Rangan et al. | ............... | 709/217 |
| 6,307,550 B1 * | 10/2001 | Chen et al. | ............... | 345/418 |
| 6,646,655 B1 * | 11/2003 | Brandt et al. | ............... | 715/723 |
| 6,647,535 B1 * | 11/2003 | Bozdagi et al. | ............... | 715/255 |
| 6,741,977 B1 * | 5/2004 | Nagaya et al. | ............... | 707/1 |
| 7,058,901 B1 * | 6/2006 | Hafey et al. | ............... | 715/792 |
| 7,313,762 B2 * | 12/2007 | Bozdagi et al. | ............... | 715/719 |
| 2002/0028026 A1 * | 3/2002 | Chen et al. | ............... | 382/284 |
| 2004/0054964 A1 * | 3/2004 | Bozdagi et al. | ............... | 715/500.1 |
| 2004/0125124 A1 * | 7/2004 | Kim et al. | ............... | 345/716 |
| 2005/0273527 A1 | 12/2005 | Olstad et al. | | |
| 2006/0064716 A1 * | 3/2006 | Sull et al. | ............... | 725/37 |
| 2007/0101266 A1 * | 5/2007 | Kim et al. | ............... | 715/719 |
| 2007/0104390 A1 * | 5/2007 | Foote | ............... | 382/284 |
| 2007/0110399 A1 * | 5/2007 | Roh | ............... | 386/95 |
| 2007/0255095 A1 * | 11/2007 | Gilreath et al. | ............... | 600/102 |
| 2009/0132588 A1 * | 5/2009 | Mahesh et al. | ............... | 707/104.1 |

OTHER PUBLICATIONS

Schmalsteig, D., et al., "Demand-Driven Geometry Transmission for Distributed Virtual Environments," Institute of Computer Graphics, 1996.
Chen, J., et al., "A Reconfigurable Architecture for Load-Balancing Rendering," Graphics Hardware 2005.
Hesina, G., et al., "A Network Architecture for Remote Rendering," Vienna University of Technology, 1998.

* cited by examiner

Primary Examiner—Aaron W Carter
(74) Attorney, Agent, or Firm—Lewis, Rice & Fingersh, L.C.

(57) ABSTRACT

A system and method for navigating an image series, the image series containing a number of substantially aligned planar images. First, the images of the image the image series are grouped into a number of subseries, the number of subseries being less than the number of substantially aligned planar images in the image series. A representative image series is generated by generating an image from each subseries. The representative image series is displayed. It is determined whether an image from the representative image series has been selected. If an image from the representative image series has been selected, then the subseries associated with the selected image is displayed.

25 Claims, 11 Drawing Sheets

STUDY NAVIGATION SYSTEM AND METHOD

FIELD

The embodiments described herein relate to image viewing and navigation systems and methods and more particularly to a system and method for navigating and viewing planar images.

BACKGROUND

Commercially available image viewing systems in the medical field utilize various techniques to present visual representations of image data to a user. Specifically, image data produced within modalities such as Computed Tomography (CT) and the like is displayed on a display terminal for review by a medical practitioner at a medical treatment site. Typically, the image data produced by the modalities is in a form of a series of planar images that are aligned along an axis that is normal to the plane of each image.

By viewing the various planar images that make up the image series, a medical practitioner can better determine the presence or absence of a medical condition (e.g. disease, tissue damage etc.). Many attempts to optimize the display and presentation of the planar image data for viewing by a medical practitioner have been made. Currently, when a medical professional wishes to review an image series that covers an area of interest, he or she must either view each image individually, or choose to skip certain images. This process can be both inefficient and prone to error. It is possible that skipping certain images in a non-systematic manner may cause the medical professional to overlook the presence of a medical condition that is reflected in one of the skipped images. For reasons such as these, it is often very difficult and time consuming for medical practitioners to review large amounts of image data.

SUMMARY

The embodiments described herein provide in one aspect, a method of navigating an image series, the image series containing a first number of substantially aligned planar images, the method comprising:

(a) grouping the images of the image series into a number of subseries, the number of subseries being less than the first number of images;

(b) generating a representative image series by generating an image from each subseries;

(c) displaying the representative image series;

(d) determining whether an image from the representative image series has been selected; and, (e) if an image from the representative image series has been selected, then displaying the subseries associated with the selected image.

The embodiments described herein provide in another aspect, a system for navigating an image series, the image series containing a first number of substantially aligned planar images, the system comprising:

(a) a memory for storing the image series;

(b) a processor coupled to the memory and configured for:

(i) grouping the images of the image series into a number of subseries, the number of subseries being less than the first number of images;

(ii) generating a representative image series by generating an image from each subseries;

(iii) displaying the representative image series;

(iv) determining whether an image from the representative image series has been selected; and, (v) if an image from the representative image series has been selected, then displaying the subseries associated with the selected image.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
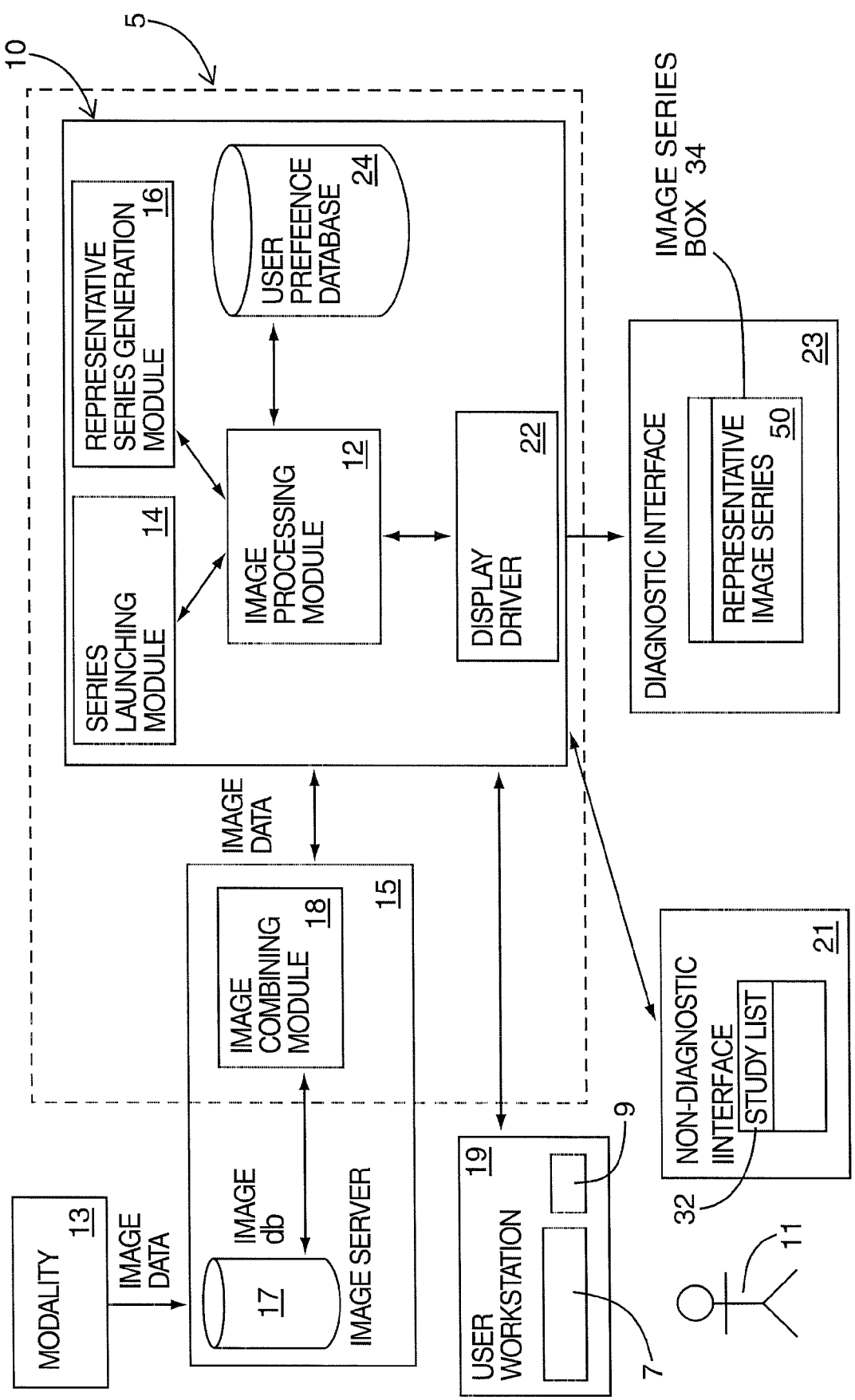
FIG. 1 is a block diagram of an exemplary embodiment of a study navigation system.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, or cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

FIG. 1 illustrates the basic elements of an exemplary embodiment of a study navigation system 5. Specifically, study navigation system 5 includes a main navigational system 10 and image combining module 18. In some embodiments, main navigational system 10 includes image combining module 18. Main navigational system 10 includes an image processing module 12, a series launching module 14, a representative series generation module 16, and a display driver 22. Thus, in various embodiments the main navigational system 10 is simply the study navigation system excluding the image combining module 18. As will be explained below some embodiments of study navigation system 5 separate the image combining module 18 in order to reduce the amount of data traffic flowing between image server 15.

As discussed in more detail above, it should be understood that study navigation system 5 may be implemented in hardware or software or a combination of both. Specifically, the modules of study navigation system 5 are preferably implemented in computer programs executing on programmable computers each comprising at least one processor, a data storage system and at least one input and at least one output device. Without limitation the programmable computers may be a mainframe computer, server, personal computer, laptop, personal data assistant or cellular telephone. In some embodiments, the modules of study navigation system 5 are implemented in software and installed on the hard drive of user workstation 19 and on image server 15, such that user workstation 19 interoperates with image server 15 in a client-server configuration. In other embodiments, the modules of study navigation system 5 can run from a single dedicated workstation that may be associated directly with a particular modality 13. In yet other embodiments, the study navigation system 5 can be configured to run remotely on the user workstation 19 while communication with the image server 15 occurs via a wide area network (WAN), such as through the Internet.

As shown, image data associated with a full image series 30 (i.e. a series of medical exam images) is generated by a modality 13 and stored in an image database 17 on an image server 15. Full image series 30 may be retrieved from image database 17 on image server 15 and displayed on diagnostic interface 23. Alternatively, a representative image series 50 may be retrieved and displayed in place of full image series 30. User 11 may review either of the above-mentioned series for a variety of reasons, including but not limited to a search for a specific pathology.

In various embodiments, user 11 is able to choose between viewing a representative image series 50 or the complete full image series 30 by entering appropriate commands as will be described below. In some embodiments, representative image series 50 is used as a shorter proxy for the full image series 30. Thus, representative image series 50 generally has fewer images than full image series 30. The use of a shorter series may allow user 11 to spend less time in reviewing the images, in order to for example determine if there is evidence of some sort of pathology. Thus, representative image series 50 allows for an alternative manner of navigating through the image data that may be more efficient as compared to simply viewing the various images of full image series 30.

In addition, in some embodiments, there is more than one type of representative image series 50. In such embodiments, certain types of representative image series 50 maybe created on image server 15 and not on main navigational system 10. Therefore, the use of a smaller representative image series rather than the larger full image series 30 means that less data must be transferred from image server 15 to main navigational system 10.

In various embodiments, representative image series 50 can be of at least two types. The first type is the selective representative image series 50a and the second type is the merged representative image series 50b. The term representative image series 50 will continue to be used to refer to both selective representative image series 50a and merged representative image series 50b when it is not necessary to differentiate between the two or to refer to either in particular. It should be understood that although only two types of representative image series are described it is not intended to exclude the use of other types of representative image series 50.

The selective representative image series 50a is made up of selected images from full image series 30. In some embodiments, selective representative image series 50a is chosen to have approximately 1/n the number of images as full image series 30. In various embodiments the images in selective representative image series 50a are chosen from approximately evenly spaced intervals in full image series 30. In such embodiments, each of the images may be chosen as every $n^{th}$ image in full image series 30.

In various embodiments, the use of selective representative image series 50a allows user 11 to view 1/n the number of images and thereby potentially save time and increase efficiency. In some embodiments, the size of selective representative image series 50a denotes the number of images in selective representative image series. Thus, the larger the number n is, the less images are present and the smaller the size of the selective image series. As will be discussed below, the size of the selective representative image series 50a is chosen in consideration of a number of factors. For example, the selective representative image series 50a is preferably small enough so as to create a navigational system for the image data that can be navigated in a relatively short time.

A second consideration is that the selective representative image series 50a is preferably large enough to avoid missing features of interest. The minimum size of a feature of interest is partially dictated by the specific application, that is, the reason behind user 11's examination of the image data. As was explained above, the underlying image data comprises a series of planar images. Each image represents a substantially parallel cross sectional image of a scanned portion of a patient. Thus, each image is spaced from an adjacent image by a given distance. Given that the selective representative image series 50a is made up of only selected images from the full image series 30, the distance between two images in selective representative image series 50a will generally be larger than in full image series 30. Thus, if user 11 is interested in a specific pathology that may be manifested in features having a given minimum size, then the representative images should be chosen such that the spacing between them is not greater than the minimum size of those features.

One way of achieving this is to ensure that selective representative image series 50a is large enough such that it includes a sufficient number of images from full image series 30 so that the spacing between any two images is smaller than the minimum size of a feature of interest. For example, if user 11 would like to make sure that he or she does not overlook a blood vessel aneurysm then the spacing between images should not be made larger than the smallest expected size of the aneurysm.

Merged representative image series 50b is made up of merged images from full image series 30. In various embodiments, the merged images are created by merging consecutive images of full image series 30. In some embodiments, each merged image of the merged representative image series 50b is generated by merging approximately the same number of images. Thus, in such embodiments, merged representative image series 50b can be chosen to have 1/n the number of images as full image series 30 by merging every n images of full image series 30 into one merged image. It is not necessary that every merged image be formed from the same number of merged images. For example, the total number of images may not be divisible by the number n and therefore at least one of the merged images may be composed of fewer images than the other merged images that make up merged representative image series 50b.

It is not intended to exclude the possibility of a representative image series 50 that is formed by merging non-consecutive images of a full images series 30. For example, but not limited to, it may be the case that a particular full image series 30 may be particularly dense and therefore the representative image series 50 may be formed by merging images spaced k images apart rather than consecutive images, where k is greater than 1. Alternatively, the images could be chosen such that they are not spaced by the same interval. Yet another alternative is to form representative image series 50 by generating an image from each subseries 52 by combining a portion of each image in the subseries 52. This could for example, but not limited to, be accomplished by ignoring certain features (or portions) during the merging process. An example of such features (or portions) could be all features (or portions) in the images having an intensity above or below a certain threshold. Alternatively, the portions or images could be selected based on their location within the image. Any appropriate method of choosing portions of the images can be utilized. As another alternative, a representative image series 50 may be formed by combining portions of only selected images in each subseries 52.

In various embodiments, the use of merged representative image series 50b allows user 11 to view less images than he or she would otherwise when viewing full image series 30. As mentioned above, in some embodiments merged representative image series 50b may comprise 1/n the number of images of full image series 30. Assuming then number of images in full image series 30 is divisible by n, this may be accomplished by merging every n images of full image series 30 into one image.

In various embodiments, each representative image series 50a and 50b has an associated subseries 52. In the case of the selective representative image series 50a, the subseries 52a is the portion of the overall full image series 30 from which the representative image is chosen. For example, if selective representative image series 50a is formed by taking every tenth image of full image series 30 then each subseries would be composed of a set of 10 consecutive images of full image series 30, assuming that the number of images in full image series 30 is divisible by 10. If the number of images is not divisible by 10 then optionally one of the subseries 52 will have less then 10 images. Alternatively, a different number other than 10 can be chosen such that the number of images in full image series 30 is either divisible by that number or is closer to being divisible by that number than by 10.

In the case of the merged representative image series 50b, the subseries 52b is the portion of the overall full image series 30 that is merged in order to create the merged image of merged representative image series 50b. For example, if merged representative image series 50b is formed by merging every ten consecutive images of full image series 30 into a single image, then each subseries 52 would be composed of a set of 10 consecutive images of full image series 30, assuming that the number of images in full image series 30 is divisible by 10. As explained above, if the number of images is not divisible by 10 then optionally one of the subseries 52 will have less then 10 images or a different number other than 10 can be chosen such that the number of images in full image series 30 is either divisible by that number or is closer to being divisible by that number than by 10.

Representative image series 50a and 50b each offer a different system and method for navigating the image data that makes up full image series 30. For example, in various embodiments, selective representative image series 50*a* consists of only a single image from each subseries. Thus, in terms of the total image information contained in the subseries, only the information present in the selected image is transferred to selective representative image series 50*a*. Thus, any other information that may not be contained in the selected image but is contained in the other images of the subseries, is not present in selective representative image series 50*a*. Thus, selective representative image series 50*a* gives user 11 a sample view of each subseries without providing all the image data in the subseries. As was explained above, each image of full image series 30 is a planar image that represents a cross-sectional view within the scanned area of a patient. In other words, each image in full image series 30 displays only those features that exist in the plane of the image. Thus, each subseries represents a series of adjacent planes. Therefore, selective representative image series 50*a* gives user 11 a view of only one of those planes from the subseries. Thus, selective representative image series 50*a* is most useful when each consecutive plane in the subseries is not significantly different than the rest of the planes within the subseries.

In contrast, in various embodiments, merged representative image series 50*b* may contain information contained in each of the images present in each subseries. This information is contained in the merged images, which are formed by superimposing a set of consecutive images according to a particular method. The amount of information that is taken from each image in the subseries depends on the method that is used to combine the images, which will be discussed in greater detail below.

Thus, in contrast to selective representative image series 50*a*, merged representative image series 50*b*, will generally provide image data from more than one image of each subseries. Specifically, as will be discussed below, depending on the method used to combine the images, each image of merged representative image series 50*b* may display features from each of the planes of the images in each subseries. In various embodiments, the images that make up merged representative image series 50*b* are projection images. Projections images are images that display features that are not necessarily coplanar. Thus, each merged image may look similar to an x-ray image, which displays features that exist in more than one plane. This is in contrast to planar cross-sectional images such as those that generally make up full image series 30.

In each of the two types of image series there is generally a tradeoff between the size of the representative image series 50 and the risk of losing potentially important detail. Thus, there are a number of criteria that may be used in determining the size of merged representative image series 50*b*. Firstly, representative image series 50 is generally made small enough in comparison to full image series 30 so that it would save a medical practitioner time to examine the representative image series 50 in place of full image series 30. A representative image series that is virtually the same size as the original full image series 30, would not generally save a medical practitioner time.

Secondly, in the case of selective image series 50*a*, each representative image is selected from a subseries of images. The smaller the selective representative image series 50*a* is, the larger the subseries is from which the representative image is selected. Generally, the larger the subseries becomes, the less likely it is that the representative image will be similar to all the images in the subseries. Thus, generally, selective representative image series 50*a* is not made so small that a significant amount of detail is skipped over between each representative image.

In the case of merged image series 50*b*, as was discussed above, each merged image is composed of several images. The smaller the merged representative image series 50*b* is, the larger the number of images that are merged into each image of the representative image series. Generally, the larger the number of images that are merged together, the more difficult it would be for user 11 to discern details in each merged image. Thus, generally, merged representative image series 50*b* is not made so small that the number of images that are merged together is so large that discerning detail becomes too difficult.

As will be explained in greater detail below, regardless of the representative image series 50*a* or 50*b* that is used, user 11 is given the option of viewing the underlying subseries associated with a particular image of the representative image series 50. This allows the user to quickly view and navigate through the image data through the use of the representative image series 50 and then "zoom" into a particular subseries for more detailed viewing and navigation.

Thus, there are a number of tradeoffs to be considered when determining the size of the representative image series. As was explained above, the size of the series impacts on how much time can be saved for user 11. If the representative image series 50 is too large, user 11 may not save much time given that he or she has to look through a large number of images. If the representative image series 50 series is too small, user may not save much time given that he or she may not be able to rely on the representative images to provide the appropriate level of detail and may therefore need to constantly go back and examine the subseries that make up each representative image of representative image series 50.

User workstation 19 includes a keyboard 7 and a user pointing device 9 (e.g. mouse) as shown in FIG. 1. It should be understood that user workstation 19 may be implemented by any wired or wireless personal computing device with input and display means (e.g. conventional personal computer, laptop computing device, personal digital assistant (PDA), wireless communication device, etc.) User workstation 19 is operatively connected to non-diagnostic interface 21 and diagnostic interface 23. As previously mentioned, study navigation system 5 is preferably installed on the hard drive of user workstation 19 and on image server 15, such that user workstation 19 interoperates with image server 15 in a client-server configuration.

Non-diagnostic interface 21 displays a study list 32 to user 11. Study list 32 also includes associated identifying indicia (e.g. body part, modality, etc.) and organizes full image series 30 and representative image series 50 in current and prior study categories. Other associated textual information (e.g. patient information, image resolution quality, date of image capture, etc.) is simultaneously displayed within study list 32 to further assist the user 11 in selection of full image series 30 and representative image series 50. Typically, user 11 will review study list 32 and select a desired listed full image series 30 or its representative image series 50 for display on diagnostic interface 23. Non-diagnostic interface 21 is preferably provided on a conventional color computer monitor (e.g. a color monitor with a resolution of 1024×768) with sufficient processing power to run a conventional operating system (e.g. Windows NT). High resolution graphics are not typically necessary for non-diagnostic interface 21 since this display is usually only displaying textual information to user 11.

Diagnostic interface 23 provides high resolution image display of full image series 30 or its representative image series 50 to user 11. Full image series 30 or its representative image series 50 can be displayed within a series box 34. Diagnostic interface 23 is preferably provided using medical imaging quality display monitor(s) with relatively high resolution typically used for viewing CT image studies (e.g. black and white "reading" monitors with a resolution of 1280-1024 and up).

Display driver 22 is a conventional display screen driver implemented using commercially available hardware and software. As shown in FIG. 1, display driver 22 ensures that full image series 30 and representative image series 50 are displayed in a proper format on diagnostic interface 23. Specifically, full image series 30 or representative image series 50 are displayed within series boxes 34. Each series box 34 contains a full image series 30 or a representative image series 50. Display driver 22 provides image data associated with full image series 30 or representative image series 50 appropriately formatted so that full image series 30 or representative image series 50 are properly displayed within one or more series boxes 34 on diagnostic interface 23.

Modality 13 is any conventional image data generating device (e.g. computed tomography (CT) scanners, etc.) utilized to generate image data that corresponds to patient medical exams. A medical practitioner utilizes the image data generated by modality 13 to make a medical diagnosis (e.g. for investigating the presence or absence of a diseased part or an injury or for ascertaining the characteristics of the diseased part or the injury). Modalities 13 may be positioned in a single location or facility, such as a medical facility, or may be remote from one another. Image data from modality 13 is stored within image database 17 within an image server 15 as conventionally known.

Image processing module 12 coordinates the activities of series launching module 14 and representative series generation module 16 in response to commands sent by user 11 from user workstation 19 and stored user launching preferences from user display preference database 24. When user 11 launches an full image series 30 from study list 32 on non-diagnostic interface 21, image processing module 12 instructs series launching module 14 to determine the type of series to be launched. For example, series launching module 14 may determine that a full image series 30 is to be launched, a selective representative image series 50a, or a merged representative image series 50b should be launched.

User 11 selects or "launches" an full image series 30 from study list 32 on non-diagnostic interface 21 using series launching module 14. The full image series 30 selected for viewing by user 11 will be referred to as the "launching series". Series launching module 14 determines whether to launch full image series 30 or a representative image series 50. When user 11 launches an full image series 30 from study list 32 on non-diagnostic interface 21, series launching module 14 determines whether to launch the actual full image series 30 or a representative image series 50. If it is determined that the full image series 30 should be launched then series launching module 14 is utilized by image processing module 12 to retrieve image data from image server 15 associated with the selected full image series 30 for display on diagnostic interface 23. If series launching module 14 determines that a representative image series 50 should be launched, then the image processing module 12 instructs representative series generation module 16 to retrieve image data that corresponds to the representative image series 50 for display on diagnostic interface 23.

Series launching module 14 allows user 11 to explicitly request whether a particular full image series 30 from study list 32 should be launched as the full image series 30 or as a representative image series 50. User 11 may also establish a default launching preference in the user preference database 24. Such launching preferences would be utilized in the case where no explicit selection of an initial launching format is made by user 11. For example, user 11 may establish a default launching preference within user preference database 24 for all full image series 30 to be initially launched as a representative image series 50. In such a case, any full image series 30 launched without an explicit launching selection made by user 11 will be launched on diagnostic interface 23 as a representative image series 50.

Series launching module 14 also provides for the ability to establish system-wide or multi-user (i.e. departmental) initial launching defaults. These kinds of initial launching defaults would preferably be applied when no explicit initial launching preferences are selected on launch and when no user default has been established. For example, a departmental launching default could be established by a CT specialty department in a hospital such that on start-up and in the absence of any user defaults or explicit user selections, an full image series 30 is launched as a representative image series 50.

Also, it should be understood that it is contemplated that series launching module 14 would monitor the initial launching selections a user 11 or a group of users 11 makes in previous imaging sessions and store related preferences in preference database 24. Accordingly, when an image series is launched, launching preferences established in a previous session would be utilized.

Representative series generation module 16 generates representative image series 50 by retrieving the appropriate images of full image series 30 from image server 15. In various embodiments, in the case of selective representative image series 50a, representative series generation module 16 may generate selective representative image series 50a by selecting every $n^{th}$ image of full image series 30 from image server 15. In the case of merged representative image series 50b, representative series generation module 16 instructs image combining module 18 to generate the merged images and then transmit them to representative series generation module 16. After obtaining the relevant image data, regardless of the type of representative image series, representative series generation module 16 then provides image processing module 12 with the images that make up representative image series 50. Image processing module 12 then instructs display driver 22 to display the representative image series 50 on diagnostic interface 23.

Image combining module 18 merges the images of full image series 30 according to the instructions provided to it by representative series generation module 16. In some embodiments, representative series generation module 16 instructs image combining module 18 to combine every n images into a single merged image. Image combining module 18 then retrieves the appropriate images from image database 17 and merges them according to any appropriate technique. Image combing module 18 then transmits the merged images to representative series generation module 16. In some embodiments, image server 15 comprises image combining module 18. In such embodiments, the images of merged representative image series 50b are combined on image server 15 before being transmitted to representative series generation module 16. Thus, in these embodiments a smaller number of images is required to be transmitted from image server 15 than would be the case if the images were combined off image server 15. This can save time and bandwidth.

Figure 2A:
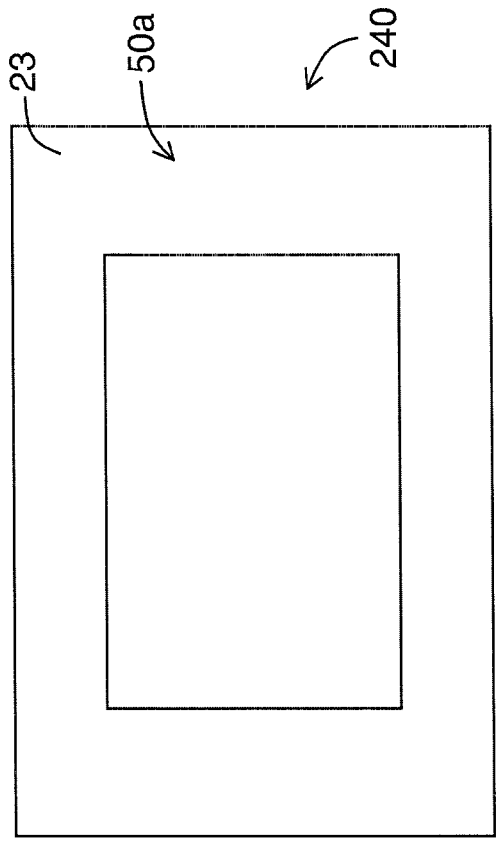
FIGS. 2A and 2B are schematic diagrams illustrating two exemplary view configurations for a selective representative image series.

FIG. 2A is a schematic diagram of the study navigation system 5 interface according to various embodiments. Specifically, one possible display configuration 220 of selective representative image series 50*a* on diagnostic interface 23 is shown. According to this display configuration 220, a number of images that make up selective representative image series 50*a* are displayed at the same time on diagnostic interface 23. In various embodiments, the number of images that are displayed may be selected by user 11 and may be changed while viewing the images. For example, user 11 may select a view of all the images of selective representative image series 50*a*, or user 11 may select a view of only a portion of selective representative image series 50*a*. Furthermore, if user 11 does not make an explicit selection, then selective representative image series 50*a* may be displayed according to default settings stored in user preference database 24.

As discussed above, these settings may have been pre-selected by user 11 or they may be set according to departmental settings. Alternatively, in some embodiments, in the absence of an explicit selection by user 11 and pre-selected defaults stored on user preferences database 24, image processing module 12, may determine an appropriate number of images to be displayed on diagnostic interface 23. Image processing module 12, may make this determination according to a number of factors including but not limited to the total number of images in representative image series 50*a*, and the size and resolution of diagnostic interface 23.

Figure 2B:
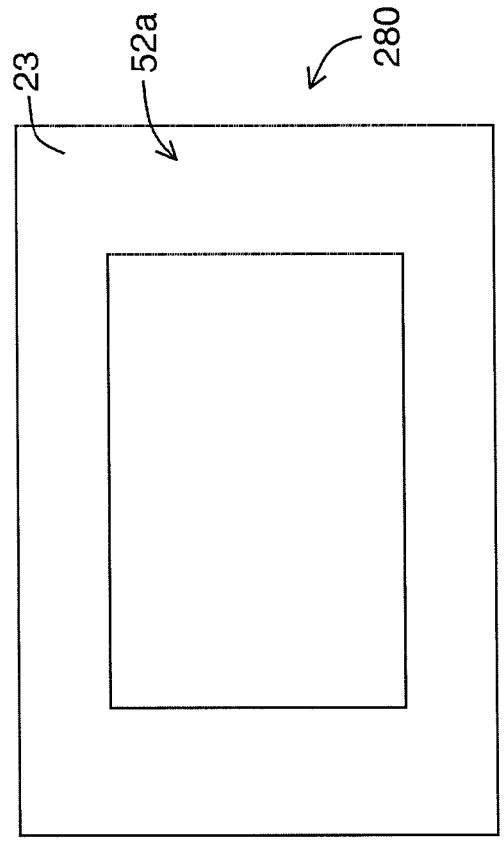

FIG. 2B is a schematic diagram of the study navigation system 5 interface according to various embodiments. Specifically, a display configuration 240 in which a single image of selective representative image series 50*a* is displayed at a time on diagnostic interface 23 is illustrated. The choice of whether to display the representative image series according to configuration 240 or configuration 220 illustrated in FIG. 2A can be made by user 11 by entering appropriate commands. As discussed above, user 11 may pre-select view settings or these settings may be set according to departmental defaults. In addition, while viewing the representative image series, user 11 may switch back and forth between either view configurations by inputting appropriate commands. For example, user 11 may use configuration 220 to quickly scan through representative image series 50*a* and use configuration 240 to view any particular image in a larger view.

Figure 2C:
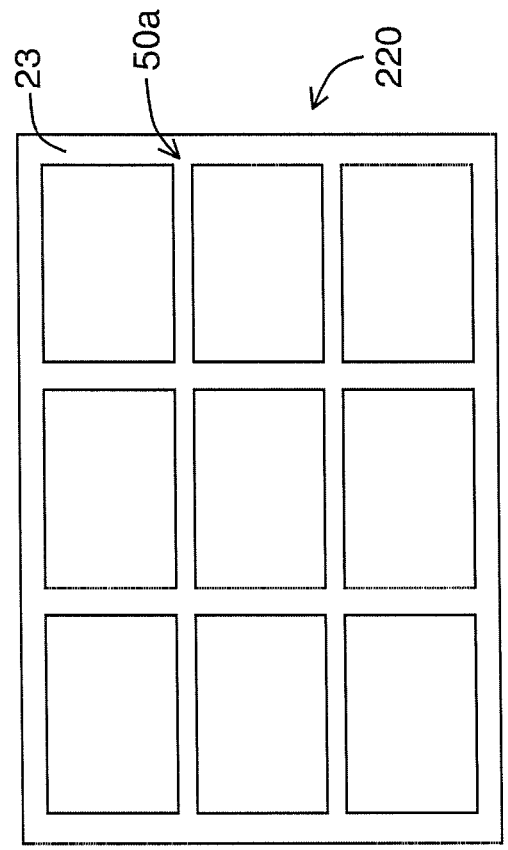
FIGS. 2C and 2D are schematic diagrams illustrating two exemplary view configurations for a subseries associated with the selective representative image series of FIGS. 2A and 2B.
Figure 2D:
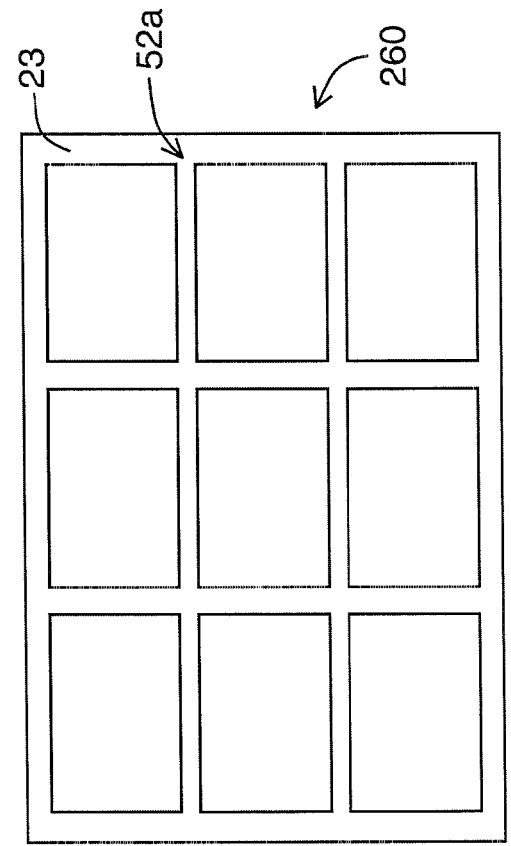

At any point while viewing selective representative image series 50*a*, user 11 may choose to view the subseries 52*a* associated with a particular image of selective representative image series 50*a*. The user may choose to view the subseries 52*a* associated with a particular image by entering in an appropriate command. FIGS. 2C and 2D each illustrate a display configuration 260 and 280, respectively. In view configuration 260 a number of images from the subseries are displayed at once on the diagnostic interface 23. In contrast, in display configuration 280 a single image of the subseries is displayed on diagnostic interface 23 at a time. The choice of which display configuration is utilized may be made by user 11. Furthermore, if user 11 does not make an explicit choice, then the display configuration may be chosen according to default settings specified in user preference database 34.

While viewing subseries 52*a*, user 11 may move between either viewing format 260 or 280 by entering appropriate commands. Furthermore, user 11 may switch back to viewing the representative image series in either viewing format 220 or 240 by entering appropriate commands. Thus, in various embodiments, user 11 may quickly switch between viewing the representative image series 50*a* and various subseries.

Figure 3A:
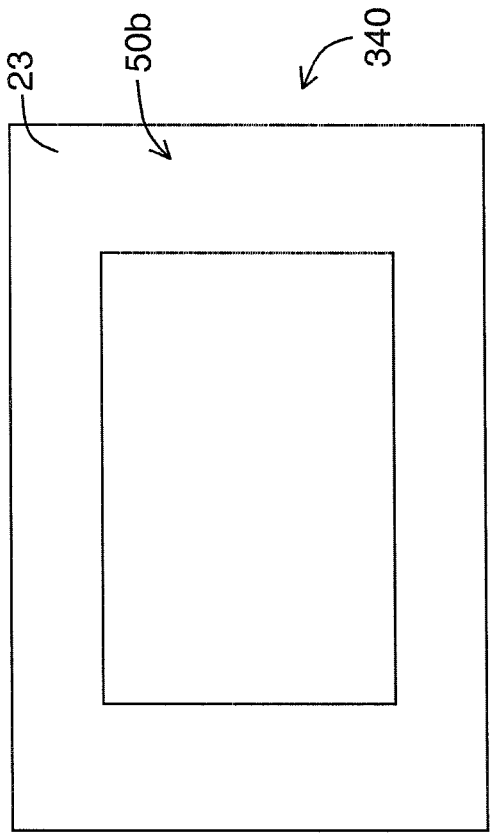
FIGS. 3A and 3B are schematic diagrams illustrating two exemplary view configurations for a merged representative image series.
Figure 3B:
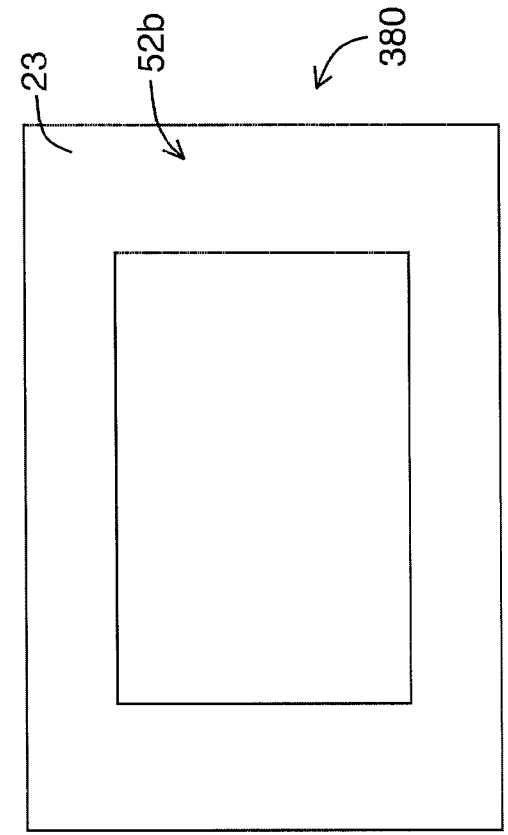
Figure 3C:
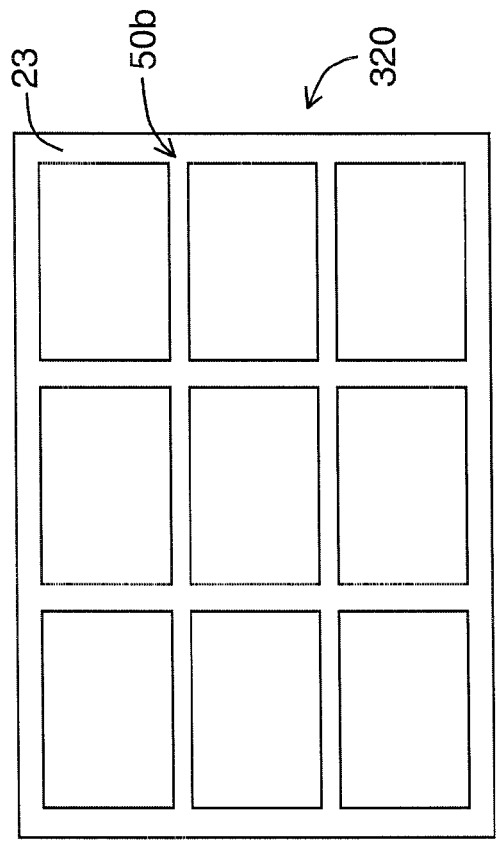
FIGS. 3C and 3D are schematic diagrams illustrating two exemplary view configurations for a subseries associated with the selective representative image series of FIGS. 3A and 3B.
Figure 3D:
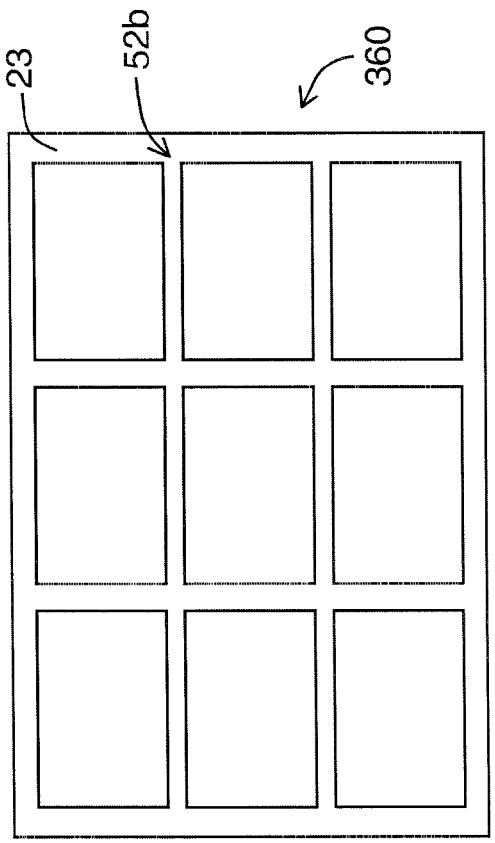

FIGS. 3A to 3D are analogous to FIGS. 2A to 2D except that they illustrate various viewing configurations for representative image series 50*b* and a subseries 52*b*. Thus, FIGS. 3A and 3B each illustrate viewing configurations 320 and 340 of merged representative image series 50*b*. Similarly, FIGS. 3C and 3D illustrate viewing configurations 360 and 380 of a particular subseries 52*b*. User 11 may switch between the various viewing configurations by entering appropriate commands as was described above. For example, if when viewing merged representative image series 50*b* through display configuration 320 user 11 selects one of the images by entering an appropriate command, then image processing module 12 will cause the appropriate subseries 52*b* to be displayed. In various embodiments, user 11 may cause this to happen by using user pointing device 9 to click on the image of merged representative image series 50*b* associated with the subseries that is to be viewed. As was explained above, in various embodiments each image of merged representative image series 50*b* is an amalgamation of the individual images in a subseries. Thus, by selecting an image of merged representative image series 50*b* in the manner described, user 11 is able to view the individual images of the subseries that were merged into the selected image of merged representative image series 50*b*.

Similar to the above, user 11 can quickly switch between view configurations 320, 340, 360, and 380 by entering appropriate commands. In this manner user 11 may quickly review the contents of an full image series 30. Specifically, user 11 may view a representative image series 50, and thereby skip over a large number of images. If user 11 notices anything of interest in a specific image, then he or she may "zoom" into the area of interest by selecting the appropriate image and viewing the associated subseries.

Figure 4A:
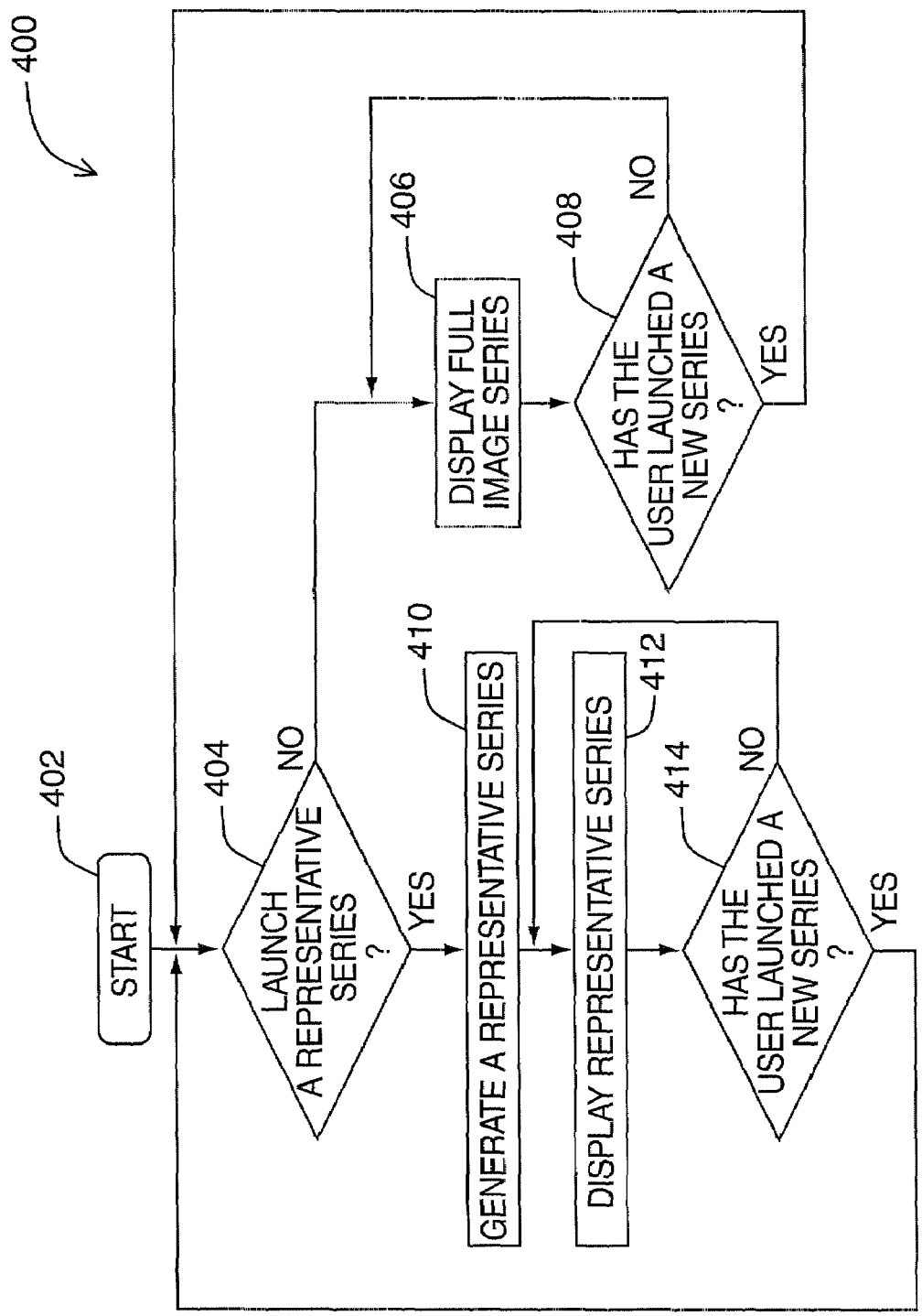
FIG. 4A is a flowchart diagram of the main operational steps executed by the study navigation system of FIG. 1 according to various embodiments.

Reference is now made to FIG. 4A, which is a flowchart diagram that illustrates the basic operational steps 400 taken by study navigation system 5 according to various embodiments.

The method starts at step (402) and is initiated when user 11 first launches a full image series 30.

At step (404), it is determined whether a representative image series 50 should be launched in place of the full image series 30. This determination can be made in a number of different ways. For example, in various embodiments user 11 may explicitly request that a representative image series 50 be used. In addition, in various embodiments series launching module 14 may make this determination based on defaults stored in user preference database 24. Alternatively, series launching module 14 may make this determination based on other criteria, such as a simple threshold. For example, if the number of images in full image series 30 exceeds the threshold then a representative image series 50 is used, otherwise the full image series 30 is launched. If a representative image series 50 is not launched, then steps (406) and (408) are executed. On the other hand if a representative image series 50 is launched, then steps (410) to (414) are executed.

At step (406), image processing module 12 causes display driver 22 to retrieve and display the full image series 30 on diagnostic interface 23. While full image series 30 is being displayed user 11 can cycle through the various images of full image series 30 and view each of them.

At step (408), it is determined whether user 11 has launched a new series. If user 11 has chosen to launch a new series, then step (404) is repeated. If user 11 has not chosen to launch a new series, then step (406) is repeated.

At step (410), representative series generation module 16 generates a representative image series 50. Upon generating the series, representative series generation module 16 provides the representative image series 50 to image processing module 12.

At step (412), image processing module 12 causes display driver 22 to display the representative image series 50 on diagnostic interface 23.

At step (414), series launching module 14 determines whether user 11 has launched a new series. If user 11 has chosen to launch a new series, then step (404) is repeated. If user 11 has not chosen to launch a new series, then step (412) is repeated.

In various embodiments, while viewing image data, user 11 can cycle between the full image series 30 and the corresponding selective representative image series 50*a* and/or the corresponding merged representative image series 50*b*. As will be explained in greater detail below, in some embodiments, study navigation system 5, uses meta-data associated with each image to link images in one series to a corresponding series (e.g. to link a particular image in full image series 30 to an image of in a representative series 50 and vice-versa. Thus, if user 11 were to switch from full image series 30 to selective representative image series 50*a*, then the meta-data associated with each image would determine which image(s) of selective representative image series 50*a* would be displayed. Similarly, if user 11 were to switch back to full image series 30, the meta-data would be used to determine which image of full image series 30 should be displayed based on the currently displayed image(s) of selective representative image series 50*a*. This allows user 11 to continue to view the same position within the body of the patient regardless of whether or not he or she switches between full image series 30 and selective representative image series 50*a* or merged representative image series 50*b*.

Figure 4B:
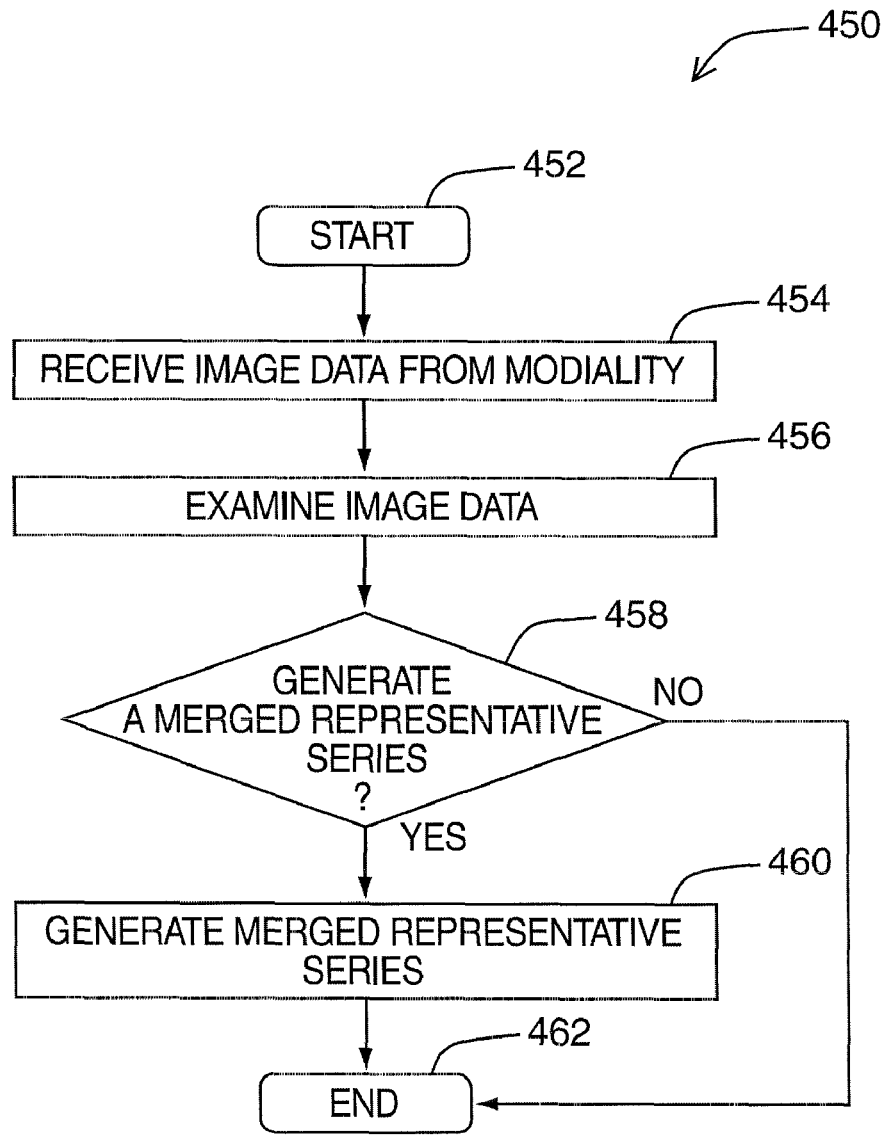
FIG. 4B is a flowchart diagram of the main operational steps executed by the study navigation system of FIG. 1 when image data is received from a modality.
Figure 4C:
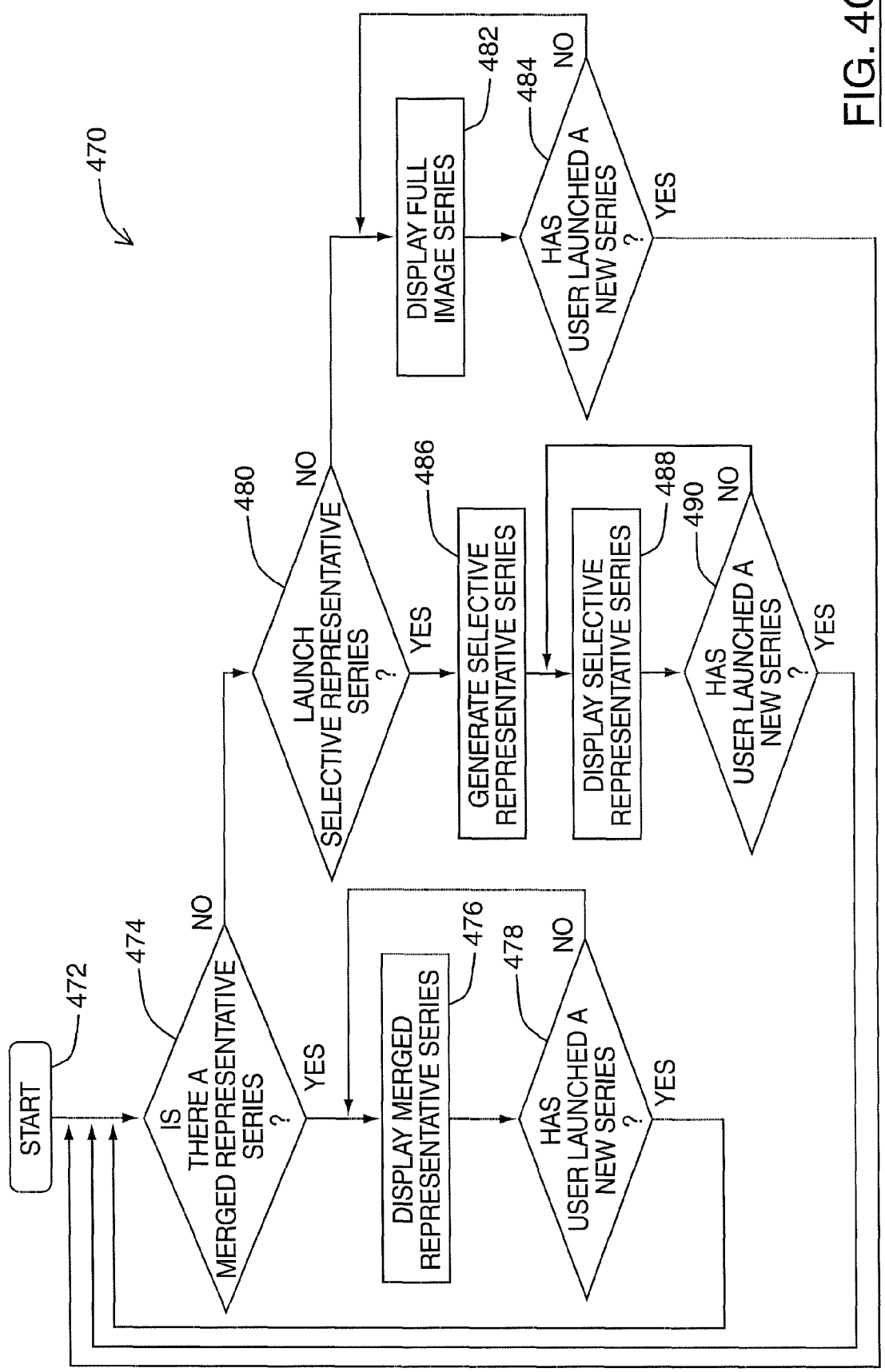
FIG. 4C is a flowchart diagram of the main operational steps executed by the study navigation system of FIG. 1 according to various embodiments.

Reference is now made to FIGS. 4B and 4C, which are flowchart diagrams that illustrates the operational steps taken by study navigation system 5 according to various alternative embodiments. These embodiments are in alternative to those embodiments for which the operational steps were illustrated in FIG. 4A. Specifically, in these alternative embodiments a decision is made as to whether merged representative image series 50*b* should be created prior to receiving a request from user 11 for image data. The process of creating a merged representative image series 50*b* may in some cases be resource and time intensive. Thus, depending on the available computing resources, an attempt to create merged representative image series 50*b* dynamically may introduce unacceptable delays in the performance of the overall system. Thus, in the alternative embodiments merged representative image series 50*b* is created beforehand in order to minimize the possibility of delay.

Reference is now made to FIG. 4B, which is a flowchart diagram that illustrates an example set of operational steps taken by study navigation system 5, according to various embodiments, when image data is received from modality 13.

The method starts at step (452) when image data is ready to be transmitted from modality 13 to image server 15. At step (454), image server 15 receives the image data from modality 13 and stores the image data in image database 17.

At step (456), image combining module 18 examines the image data received from the modality 13. At this step, image combining module 18 may examine such things as the meta-data associated with each image in the full image series 30. In addition, image combining module may determine other statistical information associated with the full image series 30 such as the total number of images in full image series 30. The meta-data may store information about the images in full image series 30 such as the position of the image relative to other images and the spacing between images. As mentioned above, each image represents a plane or slice within the body of a patient. Thus, the spacing between images refers to a measure of the distance between the planes or slices associated with the two images within the body of the patient.

At step (458), image combining module 18 determines whether a merged representative image series 50*b* should be generated. This determination is based on the examination performed in the previous step. Specifically, image combining module 18 may compare the meta-data to predefined rules. These predefined rules may be stored in user preference database 24 or elsewhere on the system. The decision as to whether to create a merged representative image series 50*b* may depend on such factors as the number of images in full image series 30. For example, in some embodiments, if the number of images in full image series 30 exceeds a predetermined threshold, then image combining module may create a merged representative image series 50*b*. If image combining module 18 determines that a merged representative image series 50*b* should be created then step (460) is executed. If not, then the method ends at step (462).

At step (460), image combining module 18 generates a merged representative image series 50*b*. Once the merged representative image series 50*b* is generated, it is stored in image database 17 on image server 15. The generation of a merged representative image series 50*b* is explained in greater detail. The manner in which image combing module 18 generates a merged representative image series 50*b* may depend on a number of factors. For example, predefined rules may be established for generating merged images that have a predetermined thickness. The thickness refers to the spacing between the first and last image of full image series 30 that were merged to create the merged image of merged representative image series 50*b*.

For example, the meta-data may reveal that each image in the full image series 30 is spaced by 1 mm and a predefined rule may be established that each image of merged representative image series 50*b* should have a thickness of 3 mm. In such a case, image combining module 18 will determine that every 3 images of full image series 30 should be combined into a single image in order to form merged representative image series 50*b*. Thus, each subseries 52*b* will comprise 3 images from full image series 30 and each image formed by merging the 3 images will have a thickness of 3 mm.

After step (460) is completed the process ends at step (462).

Reference is now made to FIG. 4C, which is a flowchart diagram that illustrates the basic operational steps 470 taken by study navigation system 5 according to various embodiments.

The method starts at step (472) and is initiated when user 11 first requests image data that is stored on image server 15.

At step (474), it is determined whether a merged representative image series 50*b* exists for the requested image data. If a merged representative image series 50*b* does exist, then step (476) is executed. On the other hand if a merged representative image series 50*b* does not exist, then step (480) is executed.

At step (476), image processing module 12 causes display driver 22 to display the merged representative image series 50*b* on diagnostic interface 23. Specifically, this is accomplished by retrieving merged representative image series 50*b*, from image server 15. As was explained above, in some embodiments, merged representative image series 50*b* is generated upon receipt of image data from modality 13 prior to user 11 requesting image data.

At step (478), series launching module 14 determines whether user 11 has launched a new series. If user 11 has chosen to launch a new series, then step (474) is repeated. If user 11 has not chosen to launch a new series, then step (476) is repeated.

Reference is now made to step (480). At step (480), it is determined whether a selective representative image series 50a should be launched in place of the full image series 30. This determination can be made in a number of different ways. For example, in various embodiments user 11 may explicitly request that a selective representative image series 50a be used. In addition, in various embodiments series launching module 14 may make this determination based on defaults stored in user preference database 24. Alternatively, series launching module 14 may make this determination based on other criteria, such as a simple threshold. For example, if the number of images in full image series 30 exceeds the threshold then a selective representative image series 50a is used, otherwise the full image series 30 is launched. If a selective representative image series 50a is not launched, then steps (482) and (484) are executed. On the other hand if a representative image series 50 is launched, then steps (486) to (490) are executed.

At step (482), image processing module 12 causes display driver 22 to retrieve and display the full image series 30 on diagnostic interface 23. While full image series 30 is being displayed user 11 can cycle through the various images of full image series 30 and view each of them.

At step (484), it is determined whether user 11 has launched a new series. If user 11 has chosen to launch a new series, then step (474) is repeated. If user 11 has not chosen to launch a new series, then step (482) is repeated.

At step (486), representative series generation module 16 generates a selective representative image series 50a. Upon generating the series, representative series generation module 16 provides the selective representative image series 50a to image processing module 12.

At step (488), image processing module 12 causes display driver 22 to display the selective representative image series on diagnostic interface 23.

At step (490), series launching module 14 determines whether user 11 has launched a new series. If user 11 has chosen to launch a new series, then step (474) is repeated. If user 11 has not chosen to launch a new series, then step (488) is repeated.

Figure 5:
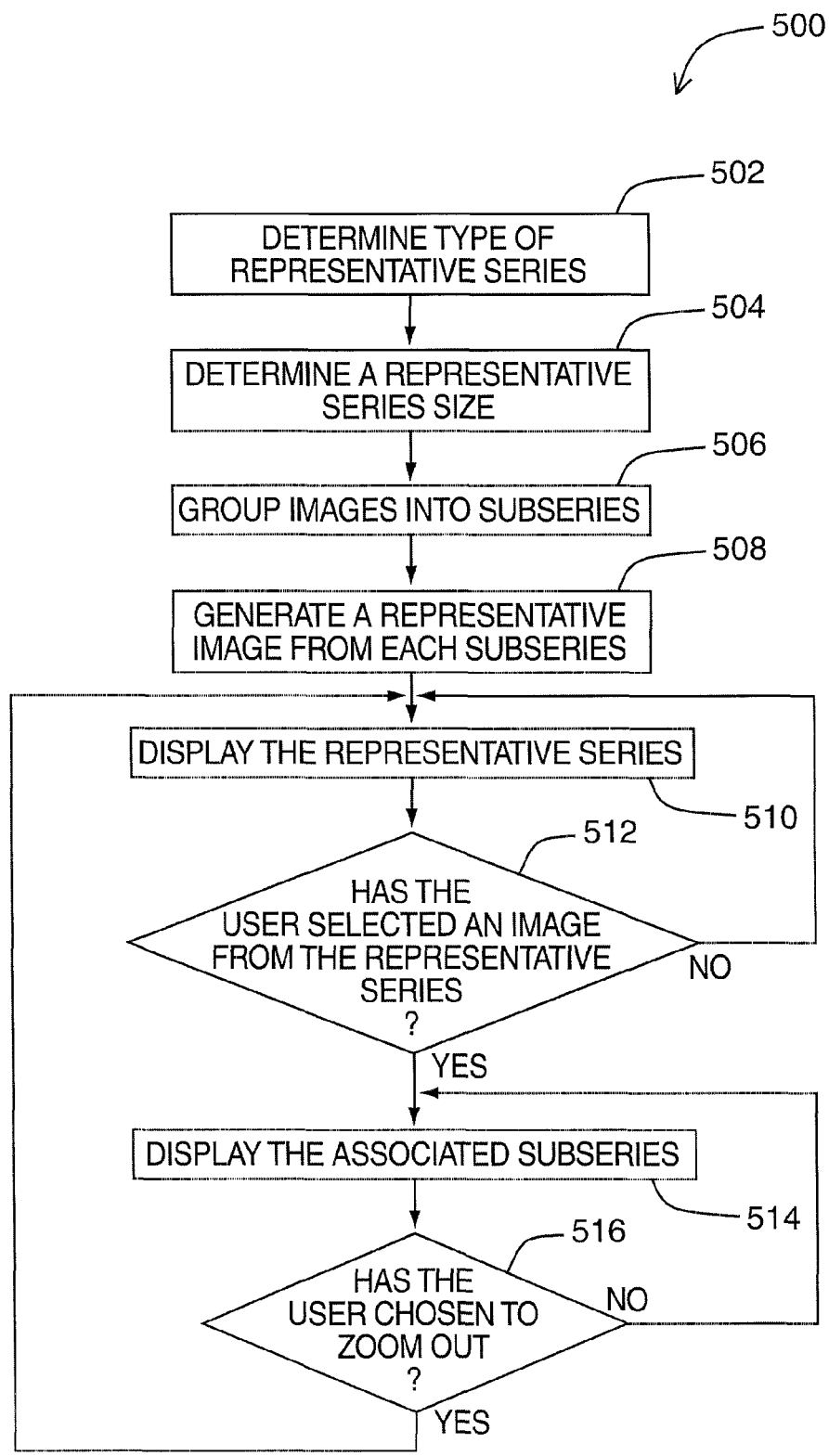
FIG. 5 is a flowchart diagram of the main operational steps executed by the representative series generation module of FIG. 1 when generating and displaying a representative image series.

Reference is now made to FIG. 5, illustrated therein is a flowchart diagram that illustrates of the basic operational steps 500 taken by study navigation system 5, when generating and displaying a representative image series.

At step (502), representative series generation module 16 determines an appropriate type of representative image series 50 for the given full image series 30. The appropriate type of representative image series 50 depends upon a number of factors including the nature of the full image series 30 and the particular application for which user 11 examines the representative image series 50.

At step (504), representative series generation module 16 determines an appropriate size for the representative image series 50 at the time image server 15 receives image data from modality 13.

At step (506), the images from the full image series 30 are grouped into a number of subseries. In various embodiments, the number of subseries is equal to the size of the representative image series 50, which was selected in the previous step. Furthermore, in some embodiments, each subseries comprises a series of consecutive images from full image series 30. Moreover, in various embodiments each subseries is roughly equal in size. However, it is not intended to exclude embodiments in which the subseries are not approximately the same size.

At step (508), a representative image is generated from each subseries. The manner in which this is achieved is dependant on the type of representative image series 50 that is created. This will be discussed in greater detail below.

As was explained above, in some embodiments steps (502) to (508) may be implemented prior to user 11 making a request for image data. In particular, in some embodiments, image combining module 18 may perform the above steps in generating a merged representative image series 50.

At step (510), image processing module 12 causes display driver 22 to display the representative image series 50 on diagnostic interface 23.

At step (512), image processing module 12 determines whether user 11 has selected an image from the representative image series 50. If user 11 has selected an image from the representative image series 50, then step (514) is executed. If user 11 has not selected an image from the representative image series 50, then step (510) is repeated.

At step (514), image processing module 12 causes display driver 22 to display the subseries associated with the selected image from the representative image series 50 on diagnostic interface 23.

At step (516), image processing module 12 determines whether user 11 has chosen to "zoom out" of the selected subseries and view the representative image series 50. If yes, then step (510) is repeated. If not, then step (514) is repeated.

In various embodiments, user 11 can alter the representative image series 50 while viewing the representative image series 50. In particular, user 11 can alter the type of representative image series 50, size of each subseries 52, as well as the manner in which the images are displayed.

Figure 6:
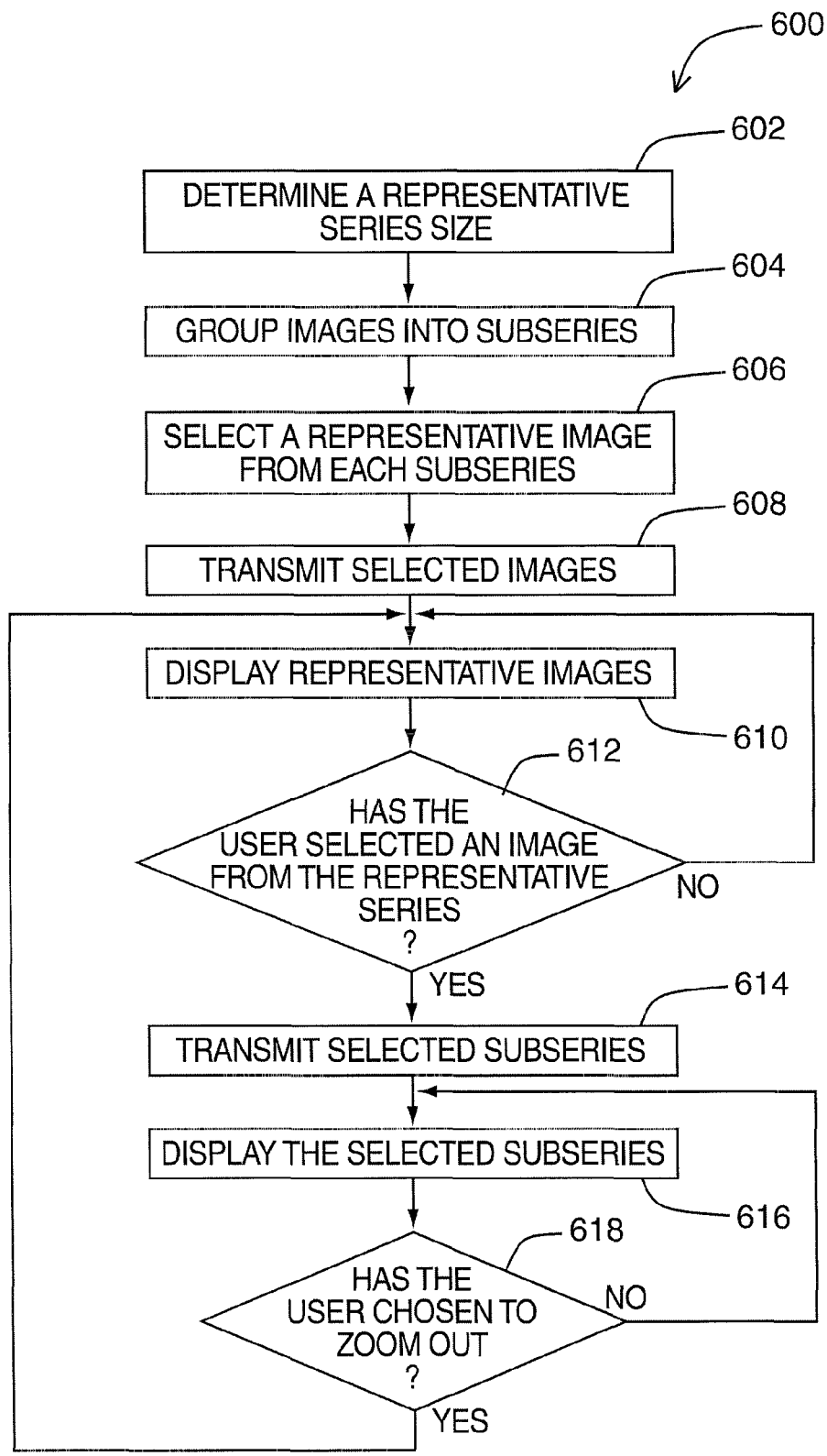
FIG. 6 is a flowchart diagram of an example set of operational steps executed by the study navigation system of FIG. 1 when generating and displaying a selective representative image series.

Reference is now made to FIG. 6, which is a flowchart diagram that illustrates the steps 600 taken by study navigation system 5, according to various embodiments of applicant's teachings, when generating and displaying selective representative image series 50a.

At step (602), image representative series generation module 16 determines an appropriate selective representative image series size. The selective representative image series size denotes the number of images in the selective representative image series 50a. In various embodiments, the selective representative image series size is chosen to be substantially smaller than the size of full image series 30. The actual selective representative image series size can be chosen by user 11 or can be a system default setting, either of which may be stored on user preference database 24. For example, the selective representative image series size may be chosen to be one tenth the size of the full image series 30.

At step (604), the images of full image series 30 are grouped into subseries. In various embodiments, each subseries is of substantially the same size. Thus, if representative image series 50a is chosen to be one-tenth the size of full image series 30, then there will be ten subseries each with approximately one-tenth of the number of images of full image series 30. Furthermore, in various embodiments each subseries is composed of approximately an equal number of consecutive images from full image series 30.

At step (606), the images that form selective representative image series 50a are selected from the subseries formed in the previous step. In various embodiments, the images that make up selective representative image series 50a are selected as the first image in each subseries. In embodiments in which the subseries are all of approximately the same size, this corresponds to choosing the images from substantially evenly spaced positions in full image series 30. Thus, if representative image series 50a is chosen to be one-tenth the size of full image series 30, then assuming that the number of images is divisible by 10, every consecutive image in representative image series 50a may correspond to every tenth image in full image series 30. However, in other embodiments the images that make up representative image series 50a are not chosen from substantially evenly spaced positions in full image series 30. Thus, it is not intended to exclude the possibility of choosing the representative image from a different position in each subseries.

The fact that only a portion of the images present in full image series 30 are viewed means that less data needs to be transmitted between the image server 15 and main navigational system 10. Specifically, it is not necessary to transmit images that are not within representative image series 50a. Thus, in the example where the representative image series 50a is one tenth the size of full image series 30, then only one tenth of the data present in full image series 30 needs to be transmitted between the image server 15 and main navigational system 10. This can save bandwidth and processing time.

At step (608), representative series generation module 16 causes the images that were selected in the previous step are transmitted from image server 15 to main navigational system 10.

At step (610), image processing module 12 causes display driver 22 to display representative image series 50a on diagnostic interface 23. In various embodiments, representative image series 50a can be displayed in a number of ways depending on the settings, which may be chosen by user 11 or stored in user preferences database 24. For example, a number of images from representative image series 50a can be displayed at one time on diagnostic interface 23 or the images can be displayed one at a time. In various embodiments, the exact number of images displayed and the manner in which they are shown on diagnostic interface 23 depends on the settings. In addition, the display settings can be altered as user 11 is viewing the images.

In some embodiments, at this step, user 11 is able to change the settings of selective representative image series 50a. In particular, user 11 can change the number of subseries 52a, or equivalently, the number of images in each subseries 52a. This would have the affect of altering the number of images that are in selective representative image series 50a. In this manner, user 11 can use an iterative approach of displaying more or less information in selective representative image series 50a. In theory, this could be used by user 11 to start with a selective representative image series 50a that has very few images and then to move to progressively larger selective representative image series 50a having a greater number of images. As more and more images are included the selective representative image series 50a comes closer and closer to the full image series 30. Eventually, the user 11 is left with the final option of display all the images of the full image series 30.

If user 11 notices something of interest in one of the images of representative image series 50a he or she may desire to view the subseries associated with that image. User 11 may view the associated subseries 52a by entering an appropriate command, which in some embodiments, may involve using user pointing device 9 to select the image of representative image series 50a. At step (612), the representative series generation module 16 determines whether user 11 has chosen to view a subseries 52a associated with particular image of representative image series 50a in greater detail. If the user has chosen to view a particular subseries 52a in greater detail then step (614) is executed. If not, then step (610) is repeated.

At step (614), representative series generation module 16 causes the selected subseries 52a to be transmitted from image server 15 to main navigational system 10. In various embodiments, the appropriate subseries 52a is selected based on the meta-data that is associated with each image of subseries 52a as well as the selected image of merged representative image series 50b. This will be explained in further detail below.

At step (616), image processing module 12 causes display driver 22 to display the selected subseries 52a of images on diagnostic interface 23. The exact manner in which this is done may be dependant on rules or settings defined on user preference database 24. For example, a particular view configuration, such as those illustrated in FIGS. 2C and 2D may be specified. This allows user 11 to examine subseries 52a in greater detail. At this point, user 11 may cycle through the images in subseries 52a and examine each image separately. It may be that user 11 had spotted a feature on the representative image that caused him or her to suspect a possible medical condition or pathology that may be displayed in this particular subseries 52a. By having the opportunity to examine each image in subseries 52a in detail he or she can confirm or dismiss his or her previous suspicion.

In various embodiments, image processing module 12 determines which image subseries 52b should be transmitted and which image(s) should be displayed at steps (614) and (616). In various other embodiments, a separate navigation module may be utilized for this purpose. The determination can be made by, for example, examining the meta-data of the particular images.

In some embodiments, at this step user 11 may cycle through and view, not just the images of the particular subseries 52a associated with the select image of selective representative image series 50a, but all the images of the full image series 30. As user 11 cycles through the images of the subseries 52a, when he or she approaches either end of the subseries 52a, images from the appropriate adjacent subseries 52a are transmitted from image database 15 so that they can be displayed. In this manner user 11 can cycle through as much of the full image series 30 as desired while only causing the desired portion of the full image series 30 to be loaded.

Thus, user 11 can avoid examining those subseries of images that do not have any indications of possible medical conditions. In this manner user 11 can save a significant amount of time by not reviewing images that do not contain relevant information. This may also be less taxing on computing resources in terms of processing power and bandwidth, given that only images in selected subseries need to be transmitted between image server 15 and main navigational system 10.

At step (618), representative series generation module 16 determines whether user 11 has chosen to stop viewing the selected series and view the selective representative image series 50a again. If yes, then step (610) is repeated. If not, then step (616) is repeated.

When step (610) is repeated, in various embodiments, image processing module 12 determines which image of full image series 30 should be displayed based on the last displayed image(s) of the subseries 52a (which are images of full image series 30) at step (616). In various other embodiments a separate navigation module may be utilized for this purpose. The determination can be made by for example, examining the meta-data of the particular images. This allows user 11 to continue to view the same position within the body of the patient regardless of whether or not he or she switches between full image series 30 and selective representative image series 50*a*. This will be explained in greater detail below.

Figure 7:
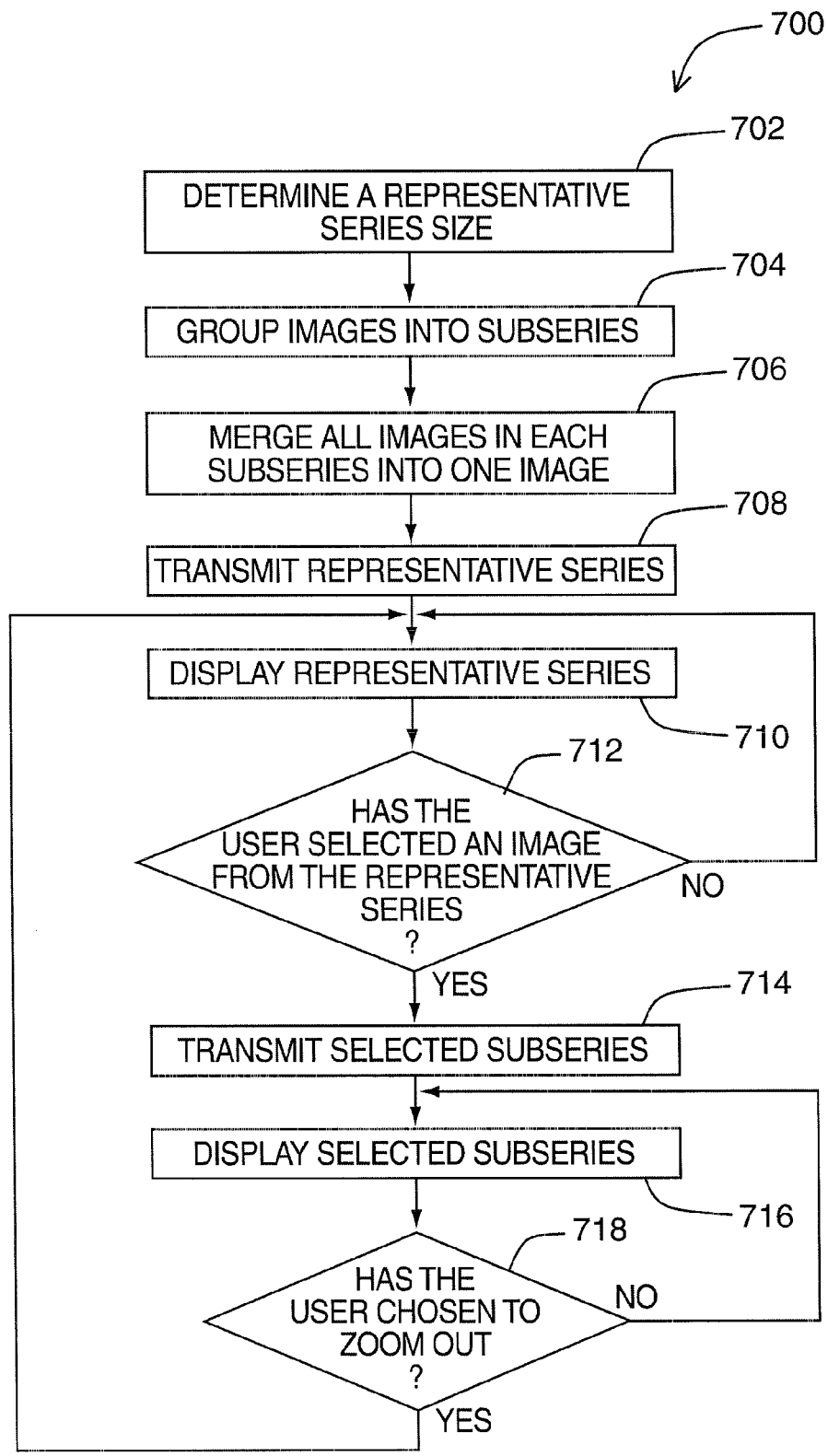
FIG. 7 is a flowchart diagram of an example set of operational steps executed by the study navigation system of FIG. 1 when generating and displaying a merged representative image series.

Reference is now made to FIG. 7, which is a flowchart diagram that illustrates the operational steps 700 according to various embodiments of applicant's teachings taken by study navigation system 5 when generating and displaying a merged representative image series 50*b*.

At step (702), representative series generation module 16 determines an appropriate merged representative image series size. In various embodiments, the size of merged representative image series 50*b* denotes the number of images in the representative image series. However, the merged representative image series size can be defined in a number of ways. For example, the size can also be defined as a ratio with respect to the size of full image series 30.

In various embodiments, the merged representative image series size is chosen to be substantially smaller than full image series 30. The actual merged representative image series size can be chosen by user 11 or can be a system default setting, either of which may be stored on user preference database 24. For example, the merged representative image series size may be chosen to be approximately one tenth the size of full image series 30. Some of the considerations made in determining the size of merged representative image series 50*b* were discussed above.

At step (704), representative series generation module 16 causes the images in full image series 30 to be divided into subseries. In various embodiments, the number of subseries is equal to the size of the merged representative image series 50*b* and each subseries is roughly of equal size. Thus, if the merged representative image series 50*b* is chosen to have a size of n images, then there will be n subseries. The subseries are formed by grouping consecutive images from the full image series 30 into each subseries. Thus, each subseries will have approximately 1/n of the total number of images present in full image series 30. Each subseries is then transmitted from image database 17 to image combining module 18.

At step (706) image combining module 18 combines the images from each subseries into one image. Any appropriate technique could be used to merge the subseries into a single image. Examples of appropriate techniques are discussed in greater detail below with respect to FIG. 8.

As was explained above in relation to FIGS. 4B and 4C, in various embodiments, merged representative image series 50*b* is created prior to receiving a request from user 11 to view image data stored on image server 15. In such embodiments, steps (702) to (706) are executed by image combining module 18 upon receipt of image data from modality 13 prior to user 11 requesting the relevant image data.

At step (708), representative series generation module 16 causes merged representative image series 50*b*, which contains each of the merged images, to be transmitted from image server 15 to main navigational system 10. In various embodiments, image combining module 18 resides on the image server. In such embodiments, only the representative image series and not the entire full image series 30 needs to be transmitted from image server 15 to main navigational system 10. Given that the representative image series is generally smaller than full image series 30, this may save time and/or bandwidth.

At step (710), image processing module 12 causes display driver 22 to display merged representative image series 50*b* on diagnostic interface 23. In various embodiments, merged representative image series 50*b* can be displayed in a number of ways depending on the settings, which may be chosen by user 11 or stored in user preferences database 24. As was discussed in relation to FIGS. 3A to 3D, a number of the merged images from merged representative image series 50*b* can be displayed at one time on diagnostic interface 23 or the images can be displayed one at a time. In various embodiments, the exact number of images displayed and the manner in which they are shown on diagnostic interface 23 depends on the settings. In addition, the display settings can be altered as user 11 is viewing the images.

In some embodiments, at this step, user 11 is able to change the settings of merged representative image series 50*b*. In particular, user 11 can change the number of subseries 52*b*, or equivalently, the number of images in each subseries 52*b*. This would have the affect of altering the number of images that are in merged representative image series 50*b* as well as the number of images that are merged to create each image of merged representative image series 50*b*. In this manner, user 11 can use an iterative approach of displaying more or less information in each image of merged representative image series 50*b*. In theory, this could be used by user 11 to start with a merged representative image series 50*b* that has very few images and each image is formed by merging a large number of images from full image series 30. User 11 can then progress to other merged representative image series 50*b* that have more and more images and each image of merged representative image series 50*b* is formed by merging fewer images from full image series 30. As more and more images are displayed, the merged representative image series 50*b* comes closer and closer to the full image series 30. Eventually, user 11 is left with the final option of display all the images of full image series 30.

If user 11 desires to view a particular merged image in the representative image series in more detail, then he or she may select that image. This allows user 11, to "zoom" into the subseries and allow him or her to view each of the images in the subseries that were merged in order to make the single merged image of merged representative image series 50*b*. At step (712), representative series generation module 16 determines whether user 11 has chosen to view a particular subseries in greater detail. User 11, may do this if he or she spots a feature that may for example represent a medical condition and therefore appears to merit further investigation. If the user has chosen to view a particular image in greater detail then step (714) is executed. If not, then step (710) is repeated.

At step (714), representative series generation module 16 causes the selected subseries 52*b* to be transmitted from image server 15 to main navigational system 10. In various embodiments, the appropriate subseries 52*b* is selected based on the meta-data that is associated with each image of subseries 52*b* as well as the selected image of merged representative image series 50*b*. This will be explained in further detail below.

At step (716) image processing module 12 causes display driver 22 to display the selected subseries 52*b* of images on diagnostic interface 23. The exact manner in which this is done may be dependant on rules or settings defined on user preference database 24. For example, a particular view configuration, such as those illustrated in FIGS. 3C and 3D may be specified. This step allows user 11 to examine the contents of merged image in greater detail, since the merged image was created from the subseries 52. At this point, user 11 may cycle through the images in the subseries 52*b* and examine each image in the subseries 52*b* separately.

In various embodiments, image processing module 12 determines which image subseries 52*b* should be transmitted and which image(s) should be displayed at steps (714) and (716). In various other embodiments, a separate navigation module may be utilized for this purpose. The determination can be made by, for example, examining the meta-data of the particular images.

In some embodiments, at this step user 11 may cycle through and view, not just the images of the particular subseries 52b associated with the select image of merged representative image series 50b, but all the images of the full image series 30. As user 11 cycles through the images of the subseries 52b, when he or she approaches either end of the subseries 52b, images from the appropriate adjacent subseries 52b are transmitted from image database 15 so that they can be displayed. In this manner user 11 can cycle through as much of the full image series 30 as desired while only causing the desired portion of the full image series 30 to be loaded.

At step (718), representative series generation module 16 determines whether user 11 has chosen to stop viewing the selected subseries and view the merged representative image series 50b again. If yes, then step (710) is repeated. If not, then step (716) is repeated.

When step (710) is repeated, in various embodiments, image processing module 12 determines which image of full image series 30 should be displayed based on the last displayed image(s) of subseries 52b (which are images from the full image series 30) at step (716). In various other embodiments a separate navigation module may be utilized for this purpose. The determination can be made by for example, examining the meta-data of the particular images. This allows user 11 to continue to view the same position within the body of the patient regardless of whether or not he or she switches between full image series 30 and selective representative image series 50a. This will be explained in greater detail below.

Figure 8:
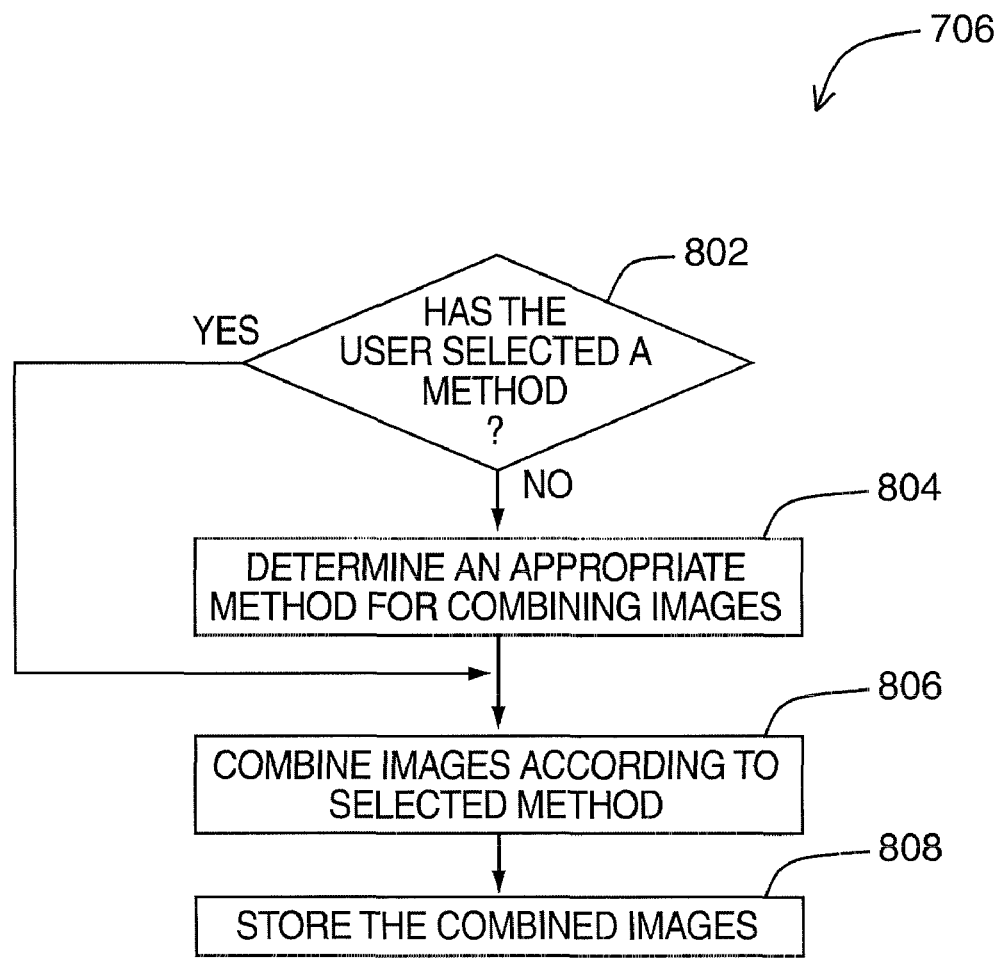
FIG. 8 is a flowchart diagram of an example set of operational steps executed by the study navigation system of FIG. 1 when combining images; and, FIG. 9 is a schematic diagram showing the relationship between a full image series and a merged representative image series.

Reference is made to FIG. 8 which is a flowchart diagram that illustrates the operational steps 706 taken by image combining module 18 when combining images of an full image series 30 to form a merged representative image series 50b.

The process begins at step (802), where image combining module 18 determines whether or not user 11 has selected a method for combining the images.

There are a number of different methods that may be used to combine the images in a subseries into a single combined image. In particular, in various embodiments, merged images are created by creating projection images. Each of these merged images, which is a projection image, may display features from each image in the associated subseries. This is possible given that projection images may display features that are not coplanar and each of the images in the associated subseries is a planar image. However, it is not necessary that features from each plane be displayed in the merged image.

There are three common methods that are used in medical imaging for creating projection images. These methods include minimum intensity projection, mean intensity projection, and maximum intensity projection. In a minimum intensity projection image, each pixel is assigned the minimum value of all the corresponding pixels in each of the images that are combined into the combined image. The term corresponding pixel is used to refer to a pixel having the same position in one image as another pixel in a different image. For example, if there are two images, image A and image B, the pixel in the bottom left corner of image A corresponds to the pixel in the bottom left corner of image B.

Similarly, when the combined image is a mean intensity projection image, each pixel of the combined image is assigned the mean value of all the corresponding pixels of the subseries images. Similarly, when the combined image is a maximum intensity projection image, each pixel of the combined image is assigned the maximum value of all the corresponding pixels of the subseries images. This example was not intended to be limiting in any manner. It is not intended to exclude other methods of combining images and various embodiments may use different methods than those that have been described above.

Typically, the method of combining images is chosen based on factors such as the specific full image series 30 and the pathology that user 11 is searching for. For example, an full image series 30 may have been created by scanning a patient who had been administered a substance that would cause his/her blood vessels to be highlighted in the resulting full image series 30. Thus, the blood vessels would have a greater intensity than other features in the full image series 30. Thus, if user 11 is interested in studying the blood vessels, a merged representative image series 50b in which maximum intensity images are used may be appropriate. As another example, if the user 11 is interested in features that may have a lower intensity than the other features of the image, as air filled structures such as lungs may have, then it may be appropriate to use minimum intensity images for the merged representative image series 50b. As a third example, if user 11 is examining the image data for a bone fractures, then mean intensity images may be appropriate.

If at step (802), user 11 has not chosen a method for combining the images, then step (804) is executed. Conversely, if at step (802), user 11 has selected a method, then step (806) is executed.

At step (804), image combining module 18, determines an appropriate method for combining the images in each subseries into a single image. In some embodiments representative series generation module 16 may make this determination instead of image combining module 18. In various embodiments, this determination may be made by using predefined settings that are stored on user preferences database 24. In some embodiments, study navigation system 5 is able to identify the type of scan. For example, this may be accomplished by storing additional information along with the full image series 30 that may identify the scan type and the original purpose for which it was taken. In addition, study navigation system 5, may be operable to determine the purpose behind user 11's examination of the image data. This can be accomplished by identifying user 11 as belonging to a specific type of user such as a lung specialist. In such a case image combining module 18 may determine that purpose of the examination is to examine lungs and that minimum intensity images are appropriate.

Alternatively, in various embodiments, equivalent information may be stored on user preference database 24. In some embodiments, study navigation system 5 does not make these determinations but rather leaves it to user 11 to make these determinations and therefore step (804) is not executed. In various embodiments, after making a determination of which method to use study navigation system 5 may suggest a method to user 11 and allow him or her to either confirm the choice or make a different selection.

At step (806), image combining module 18 combines each image in each subseries into a single combined image according to the selected method. The combined images make up merged representative image series 50b.

At step (808), image combining module 18 causes each of the combined images that make up merged representative image series 50b to be stored. In some embodiments, the merged representative image series 50b is only temporarily stored until it is transmitted to main navigational system 10. Once merged representative image series 50b has been transmitted, then it is deleted from the image server. In other embodiments merged representative image series 50b is optionally stored for use in subsequent sessions.

Figure 9:
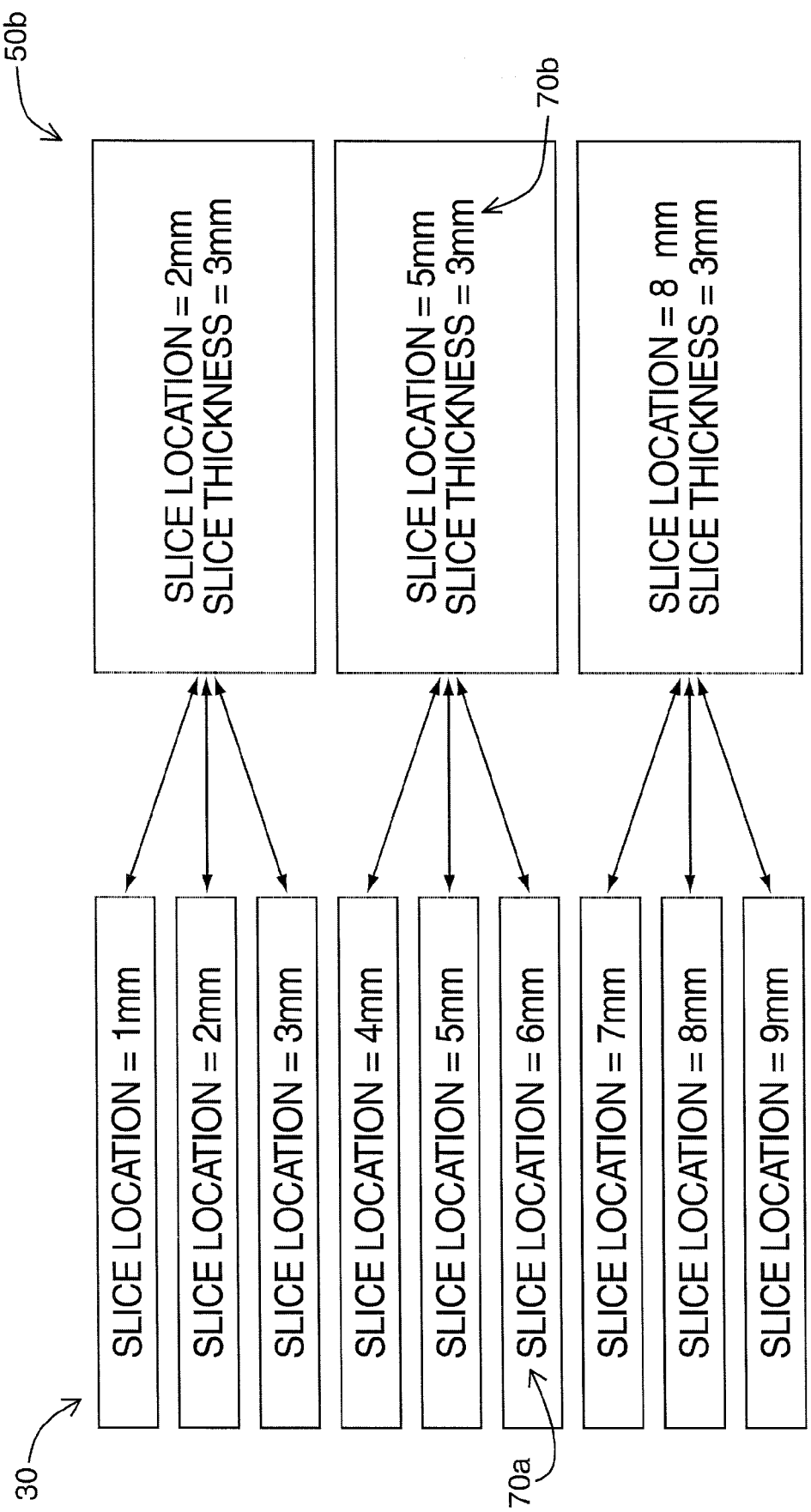

Reference is now made to FIG. 9, which is a schematic diagram showing the relationship between a full image series 30 and a merged representative image series 50b. Normally, each of the full image series 30 and merged representative image series 50b would comprise a larger number of images. However, the number of images has been purposefully kept low in order to provide greater clarity.

FIG. 9 illustrates a situation in which every 3 consecutive images of full image series 30 is combined into a single merged image of merged representative image series 50b. As shown each image, of full image series 30 has meta-data 70a associated with it. Specifically, meta-data 70a indicates the location of the image. It is not intended to exclude the possibility of other information also being contained in meta-data 70a. As mentioned above, each image of full image series 30 represents a plane or slice of a subject patient. Thus, meta-data 70a specifies the position of each image of full image series 30 relative to the other images of full image series 30.

Similarly, each image of merged representative image series 50b has meta-data 70b associated with it. Meta-data 70b indicates the thickness of the merged image. The thickness refers to the distance between the first and last plane illustrated in the particular image of combined representative image series 50b. The thickness can also be described as the distance between the first and last image used to create the merged image of merged representative image series 50b. Meta-data 70b also contains information that would point to an image of the full image series 30. The image that is pointed to is within the subseries 52b that is used to create the merged representative image series 30. This information is used to select an image that is to be displayed when, for example, at step (716) of FIG. 7 the subseries is displayed. The choice determines which image of all the images in subseries 52b will be displayed if for example, the view configuration is set to display only a single image of subseries 52 such as view configuration 380 of FIG. 3D.

Consider the following example, which refers to both FIGS. 7 and 9. In this example, the user preferences stored on user preferences database 24 specify a view configuration in which only a single image is displayed at a time on diagnostic interface 23. At step (710) of FIG. 7, user 11 views the merged representative image series 50b of FIG. 9. At step (712) of FIG. 7 it is determined that user 11 has selected the first image of merged representative image series 50b of FIG. 9. This causes the second image of full image series 30 of FIG. 9 to be displayed at step (716). Of course, if the view configuration were set to display 3 images of subseries 52b then all three images would be displayed.

The meta-data 70a and 70b is also utilized in order to determine which image of merged representative image series 50b (or the full image series 30) should be displayed when switching from viewing subseries 52b to viewing the merged representative image series 50b. Consider the following example, which refers to both FIGS. 7 and 9. User 11 views the first image of merged representative image series 50b of FIG. 9. At step (712) of FIG. 7, it is determined that user 11 selected the first image of merged representative image series 50b of FIG. 9. This causes the second image of full image series 30 to be displayed (along with possibly other images depending on the view settings) at step (716). During step (716), user 11 cycled through the images of full image series 30 and stopped at the sixth image of full image series 30 shown in FIG. 9. Then at step (718), it is determined that user 11 has chosen to zoom out of viewing the images of full image series 30 and view the merged representative image series 30. Thus, after step (718), step (710) is executed and based on the meta-data 70a and 70b image processing module 12 displays the second image of merged representative image series 50b.

Thus the use of meta-data in the various images ensures that a user's position in an image series is substantially preserved regardless of the switching between types of image series (e.g. between full image series 30 and merged representative image series 50b). In other words, user 11 may locate a given position of the body in on series (e.g. full image series 30) and then switch to another series (e.g. merged representative image series 50b) and still be in the same position of the body. Therefore, user 11 does not have to find his or her place each time he or she switches between different types of series.

Although FIG. 9 has been illustrated and explained with respect to a merged representative image series 50b, an analogous relationship between a selective representative image series 50a and a full image series 30 is possible. Specifically a selective representative image series 50a can contain similar meta-data, which would allow for similar switching between the selective representative image series 50a and a full image series 30 is possible.

While the various exemplary embodiments of the study navigation system 5 have been described in the context of medical image management in order to provide an application-specific illustration, it should be understood that study navigation system 5 could also be adapted to any other type of image or document display system.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A method of navigating an image series, the method comprising:
   (a) providing an image series containing a first number of planar images, the planar images comprising slices spatially aligned along an axis normal to the plane of each image;
   (b) storing the image series on a server;
   (c) grouping the images of the image series into a number of subseries, the number of subseries being less than the first number of images;
   (d) generating a representative image series by generating an image from each subseries;
   (e) transmitting the representative image series from the server to a client computing device;
   (f) displaying the representative image series on a display;
   (g) determining whether an image from the representative image series has been selected; and,
   (h) if an image from the representative image series has been selected, then transmitting the subseries associated with the selected image to the client computing device.

2. The method as defined in claim 1, wherein each subseries comprises a set of consecutive images from the image series.

3. The method as defined in claim 1, wherein (d) comprises generating the representative image series by generating an image from each subseries by selecting an image from each subseries.

4. The method as defined in claim 1, wherein (d) comprises generating the representative image series by generating an image from each subseries by merging the consecutive images of the subseries into a single merged image.

5. The method as defined in claim 4, wherein the merged images are projection images.

6. The method as defined in claim 1, further comprising:
   (i) selecting a threshold;
   (j) determining whether the first number is above the threshold;

(k) if the first number is above the threshold then performing (c) through (h), otherwise displaying the image series.

7. The method as defined in claim 1, further comprising:
(i) displaying the subseries;
(ii) determining whether to end the display of the subseries; and
(iii) if it has been determined to end the display of the subseries then re-performing (f).

8. The method as defined in claim 1, wherein at least one of:
A) each image of the representative image series comprises representative image series meta-data, wherein the representative image series meta-data defines associated subseries; and
B) each image of each subseries comprises subseries meta-data, wherein the subseries meta-data defines an associated image of the representative images series.

9. The method as defined in claim 1, wherein (f) comprises:
receiving a request for image data from a user; and
displaying the representative image series after receiving the request from the user.

10. The method as defined in claim 9, wherein (c) and (d) are performed before (f).

11. The method as defined in claim 1, wherein (d) comprises generating the representative image series by generating an image from each subseries by:
(A) selecting a number of imaged images from the subseries; and
(B) merging the selected images into a single image.

12. The method as defined in claim 1, wherein (d) comprises generating the representative image series by generating an image from each subseries by one of
A)
(I) selecting a portion of each image from the subseries; and,
(II) merging the selected portions of images into a single image;
and
B)
(i) selecting a number of images from the subseries;
(ii) selecting a portion of each selected image; and,
(iii) merging the selected portions of the selected images into a single image.

13. A non-transitory computer-readable medium upon which a plurality of instructions are stored, the instructions for performing the steps of the method as claimed in claim 1.

14. A system for navigating an image series, the system comprising:
(a) a server for storing the image series;
(b) a processor coupled to the server, the they system configured for:
(i) providing an image series containing a first number of planar images, the planar images comprising slices spatially aligned along an axis normal to the plane of each image;
(ii) grouping the images of the image series into a number of subseries, the number of subseries being less than the first number of images;
(iii) generating a representative image series by generating an image from each subseries;
(iv) transmitting the representative image series from the server to the processor;
(v) displaying the representative image series on a display;
(vi) determining whether an image from the representative image series has been selected; and,
(vii) if an image from the representative image series has been selected, then transmitting the subseries associated with the selected image to the processor.

15. The system as defined in claim 14, wherein each subseries comprises a set of consecutive images from the image series.

16. The system as defined in claim 14, wherein (iii) comprises generating the representative image series by generating an image from each subseries by selecting an image from each subseries.

17. The system as defined in claim 14, wherein (iii) comprises generating the representative image series by generating an image from each subseries by merging the consecutive images of the subseries into a single merged image.

18. The system as defined in claim 17, wherein the merged images are projection images.

19. The system as defined in claim 14, further comprising:
(A) selecting a threshold;
(B) determining whether the first number is above the threshold;
(C) if the first number is above the threshold then performing (ii) through (vii), otherwise displaying the image series.

20. The system as defined in claim 14, further comprising:
(I) displaying the subseries;
(II) determining whether to end the display of the subseries; and
(III) if it has been determined to end the display of the subseries then re-performing (v).

21. The system as defined in claim 14, wherein at least one of:
A) each image of the representative image series comprises representative image series meta-data, wherein the representative image series meta-data defines the associated subseries; and
B) each image of each subseries comprises meta-data, wherein the subseries meta-data defines an associated image of the representative images series.

22. The system as defined in claim 14, wherein (v) comprises:
(A) receiving a request for image data from a user; and
(B) displaying the representative image series after receiving the request from the user.

23. The system as defined in claim 22, wherein (ii) and (iii) are performed before (v).

24. The system as defined in claim 14, wherein (iii) comprises generating the representative image series by generating an image from each subseries by:
(I) selecting a number of images from the subseries; and,
(II) merging the selected images into a single image.

25. The system as defined in claim 14, wherein (iii) comprises generating the representative image series by generating an image from each subseries by one of:
1)
(A) selecting a portion of each image from the subseries; and,
(B) merging the selected portions of images into a single image;
and
2)
(I) selecting a number of images from the subseries;
(II) selecting a portion of each selected image; and,
(III) merging the selected portions of the selected images into a single image.

* * * * *